United States Patent
Abhishek et al.

(10) Patent No.: US 9,909,968 B2
(45) Date of Patent: Mar. 6, 2018

(54) METHODS, DEVICES, AND SYSTEMS FOR MEASURING PHYSICAL PROPERTIES OF FLUID

(71) Applicant: Abram Scientific, Inc., Pleasant Hill, CA (US)

(72) Inventors: Ramkumar Abhishek, Mountain View, CA (US); Norimasa Yoshimizu, Pleasant Hill, CA (US)

(73) Assignee: ABRAM SCIENTIFIC, INC., Pleasant Hill, CA (US)

( * ) Notice: Subject to any disclaimer, the term of this patent is extended or adjusted under 35 U.S.C. 154(b) by 0 days.

(21) Appl. No.: 15/343,841

(22) Filed: Nov. 4, 2016

(65) Prior Publication Data

US 2017/0059464 A1 Mar. 2, 2017

Related U.S. Application Data

(62) Division of application No. 13/742,244, filed on Jan. 15, 2013, now Pat. No. 9,518,905.
(Continued)

(51) Int. Cl.
*G01N 11/16* (2006.01)
*G01N 29/02* (2006.01)
(Continued)

(52) U.S. Cl.
CPC ............ *G01N 11/16* (2013.01); *G01N 29/02* (2013.01); *G01N 29/022* (2013.01);
(Continued)

(58) Field of Classification Search
CPC ...... G01N 11/16; G01N 29/02; G01N 29/022; G01N 29/036; G01N 33/48707;
(Continued)

(56) References Cited

U.S. PATENT DOCUMENTS 3,766,774 A 10/1973 Clark
4,166,381 A 9/1979 Woo
(Continued)

FOREIGN PATENT DOCUMENTS

EP 0 400 939 A2 5/1990
EP 1 004 882 A2 5/2000
(Continued)

OTHER PUBLICATIONS

Shah et al., "Modeling a Piezoelectric TSM Sensor to study Kinetics of Multi-layer Biosensing Structure", 2004, IEEE/EMBS International Summer School on Medical Devices and Biosensors (ISSS-MD), pp. 12-16.*
(Continued)

*Primary Examiner* — Hezron E Williams
*Assistant Examiner* — Marrit Eyassu
(74) *Attorney, Agent, or Firm* — Finnegan, Henderson, Farabow, Garrett & Dunner, LLP

(57) ABSTRACT

Disclosed herein are devices for measuring, at one or more time points, one or more properties or changes in properties of a fluid sample. The devices may comprise a chamber defining an internal volume of the device suitable for receiving and retaining the fluid sample; a plurality of layers, the plurality comprising at least a first layer below the chamber, at least a second layer above the chamber, and a substrate layer between the first and second layers, wherein: the substrate layer is linked to at least one suspended element located within the chamber; the suspended element is linked to the substrate layer by at least two compliant structures located within the chamber; and the suspended element is configured to oscillate upon application of an actuating signal to at least one electrically conductive path, which runs across at least two of the compliant structures and the suspended element. Related methods and uses are also disclosed.

7 Claims, 13 Drawing Sheets

Related U.S. Application Data

(60) Provisional application No. 61/587,020, filed on Jan. 16, 2012.

(51) Int. Cl.
*G01N 29/036* (2006.01)
*G01N 33/487* (2006.01)
*G01N 33/49* (2006.01)

(52) U.S. Cl.
CPC ..... *G01N 29/036* (2013.01); *G01N 33/48707* (2013.01); *G01N 33/4905* (2013.01); *G01N 2291/02466* (2013.01); *G01N 2291/02818* (2013.01)

(58) Field of Classification Search
CPC ..... G01N 33/4095; G01N 2291/02466; G01N 2291/02818
USPC ...................................................... 73/54.41
See application file for complete search history.

(56) References Cited

U.S. PATENT DOCUMENTS

| | | |
|---|---|---|
| 4,341,111 A | 7/1982 | Husar |
| 4,429,564 A | 2/1984 | Ikeda et al. |
| 4,862,384 A | 8/1989 | Bujard |
| 4,905,499 A | 3/1990 | Miura et al. |
| 4,920,787 A | 5/1990 | Dual et al. |
| 5,146,787 A | 9/1992 | Thomas et al. |
| 5,201,215 A | 4/1993 | Granstaff et al. |
| 5,211,054 A | 5/1993 | Muramatsu et al. |
| 5,302,878 A | 4/1994 | Soucemarianadin et al. |
| 5,334,303 A | 8/1994 | Muramatsu et al. |
| 5,372,946 A | 12/1994 | Cusak et al. |
| 5,418,141 A | 5/1995 | Zweig et al. |
| 5,494,639 A | 2/1996 | Grzegorzewski |
| 5,526,111 A | 6/1996 | Collins et al. |
| D371,605 S | 7/1996 | Wong et al. |
| 5,533,381 A | 7/1996 | Seale |
| 5,565,620 A | 10/1996 | Bohlin |
| 5,580,744 A | 12/1996 | Zweig |
| 5,628,961 A | 5/1997 | Davis et al. |
| 5,795,993 A * | 8/1998 | Pfeifer ................. G01N 29/022 73/24.01 |
| 5,832,921 A | 11/1998 | Lennert et al. |
| 5,837,885 A | 11/1998 | Goodbread et al. |
| 5,841,023 A | 11/1998 | Parker et al. |
| 5,886,252 A | 3/1999 | Lennert et al. |
| 5,889,351 A | 3/1999 | Okumura et al. |
| 6,023,961 A | 2/2000 | Discenzo et al. |
| D435,020 S | 12/2000 | Zweig et al. |
| 6,171,237 B1 | 1/2001 | Avitall et al. |
| D438,971 S | 3/2001 | Meyer et al. |
| 6,198,950 B1 | 3/2001 | Kraus |
| 6,200,532 B1 | 3/2001 | Wu et al. |
| 6,269,686 B1 | 8/2001 | Hahn et al. |
| 6,397,661 B1 | 6/2002 | Grimes et al. |
| 6,448,024 B1 | 9/2002 | Bruegger |
| 6,575,900 B1 | 6/2003 | Zweig |
| 6,629,057 B2 | 9/2003 | Zweig et al. |
| 6,668,621 B1 | 12/2003 | Wright |
| 6,673,622 B1 | 1/2004 | Jina |
| 6,688,176 B2 | 2/2004 | Storm, Jr. et al. |
| 6,699,718 B1 | 3/2004 | Bruegger |
| 6,709,390 B1 | 3/2004 | Pop |
| 6,771,081 B2 | 8/2004 | Borwick, III et al. |
| 6,800,488 B2 | 10/2004 | Khan et al. |
| 6,830,934 B1 | 12/2004 | Harding et al. |
| 6,849,456 B2 | 2/2005 | Patel et al. |
| 6,907,772 B2 | 6/2005 | Kensey et al. |
| 6,908,593 B1 | 6/2005 | Shartle |
| 6,938,462 B2 | 9/2005 | Jakoby et al. |
| 7,002,281 B2 | 2/2006 | Andle |
| 7,059,176 B2 | 6/2006 | Sparks |
| 7,117,721 B2 | 10/2006 | Neel et al. |
| 7,131,342 B2 | 11/2006 | Hodges |
| 7,191,667 B2 | 3/2007 | Wenger et al. |
| 7,207,939 B2 | 4/2007 | Husher |
| 7,235,213 B2 | 6/2007 | Mpock et al. |
| 7,263,874 B2 | 9/2007 | Fitch et al. |
| 7,290,441 B2 | 11/2007 | Baek |
| 7,328,604 B2 * | 2/2008 | DeNatale ........... G01N 33/2888 73/53.01 |
| 7,329,932 B2 | 2/2008 | DeNatale et al. |
| 7,458,265 B2 | 12/2008 | Shih et al. |
| 7,552,619 B2 | 6/2009 | Andle |
| 7,674,616 B2 * | 3/2010 | Farnam ................... C12Q 1/56 422/50 |
| 7,727,467 B2 | 6/2010 | Burke et al. |
| 7,745,224 B2 | 6/2010 | Zander et al. |
| 7,758,505 B2 | 7/2010 | Fine et al. |
| 7,770,436 B2 | 8/2010 | Baek |
| 7,775,084 B2 | 8/2010 | Huq et al. |
| 7,775,976 B2 | 8/2010 | Fuller et al. |
| 7,874,199 B2 | 1/2011 | Chaudoreille et al. |
| 7,879,615 B2 | 2/2011 | Kautzky |
| 7,879,618 B2 | 2/2011 | Mosoiu et al. |
| 7,922,985 B2 | 4/2011 | Mahoney et al. |
| 8,166,801 B2 | 5/2012 | Sinha |
| 8,166,812 B2 | 5/2012 | Desroques et al. |
| 8,173,008 B2 | 5/2012 | Leong |
| 8,178,313 B2 | 5/2012 | Mahoney et al. |
| 8,187,658 B2 | 5/2012 | Mahoney et al. |
| 8,197,418 B2 * | 6/2012 | Lal ...................... A61B 5/0053 600/552 |
| 8,210,030 B2 | 7/2012 | Djakov et al. |
| 8,215,156 B2 | 7/2012 | Miura |
| 8,272,274 B2 | 9/2012 | Sparks et al. |
| 8,277,384 B2 | 10/2012 | Fine |
| 2004/0087836 A1 | 5/2004 | Green et al. |
| 2006/0035298 A1 | 2/2006 | Hill et al. |
| 2009/0120168 A1 | 5/2009 | Harrison et al. |
| 2010/0015649 A1 * | 1/2010 | Day ..................... G01N 9/002 435/13 |
| 2010/0252452 A1 | 10/2010 | Newman et al. |
| 2010/0332155 A1 | 12/2010 | Puchades et al. |
| 2011/0020785 A1 | 1/2011 | Lowery, Jr. et al. |
| 2011/0039285 A1 | 2/2011 | Sadaba Champetier De Ribes et al. |
| 2011/0040572 A1 | 2/2011 | Chmiel et al. |
| 2011/0061462 A1 | 3/2011 | Ichihashi et al. |
| 2011/0129929 A1 | 6/2011 | Day et al. |
| 2011/0151491 A1 | 6/2011 | Dennis et al. |
| 2011/0312002 A1 | 12/2011 | Taktak et al. |
| 2012/0152001 A1 | 6/2012 | Reichel et al. |
| 2012/0239314 A1 | 9/2012 | Kurauchi et al. |

FOREIGN PATENT DOCUMENTS

| | | |
|---|---|---|
| EP | 0 717 838 | 5/2004 |
| EP | 1 588 161 | 10/2007 |
| GB | 2180691 A | 4/1987 |
| GB | 2478225 | 8/2011 |
| JP | 62063828 A | 3/1987 |
| JP | 03148878 A | 6/1991 |
| JP | 04233280 A | 8/1992 |
| JP | 08293615 A | 11/1996 |
| JP | 2000-161962 A | 6/2000 |
| JP | 2004527747 A | 9/2004 |
| WO | WO 2002/077613 A2 | 10/2002 |
| WO | WO 2008/081181 | 7/2008 |
| WO | WO 2012/009550 | 1/2012 |

OTHER PUBLICATIONS

Frieder Lucklum et al., "Miniature density-viscosity measurement cell utilizing electrodynamic-acoustic resonator sensors", 2011, Sensors and Actuators A: Physical, pp. 75-81.*

Chinese Patent Application No. 201380013950.1, by Abram Scientific, Inc.; First Office Action, dated Mar. 4, 2016, with English Translation.

(56) References Cited

OTHER PUBLICATIONS

Chinese Patient Application No. 201380013950.1, by Abram Scientific, Inc.; Search Report, dated Feb. 24, 2016, EnglishTranslation.
Japanese Patent Application No. 2014-552385, by Abram Scientific, Inc.; First Office Action, dated Dec. 6, 2016, with English Translation.
Frieder Lucklum et al., "Miniature density-viscosity measurement cell utilizing electrodynamic-acoustic resonator sensors", Sensors and Actuators A: Physical, Feb. 25, 2011, pp. 75-81.
Bandey et al., "Blood rheological characterization using the thickness-shear mode resonator," *Biosensors and Bioelectronics*, 19: 1657-1665 (2004).
Day, Highland Bioscience Ltd., "Towards a new diagnostic for cattle TB," slide deck dated Apr. 18, 2012, 15 pages.
Jakoby et al., "An Automotive Engine Oil Viscosity Sensor," *IEEE Sensors Journal*, 3(5): 562-568 (2003).
Lowe, "Blood rheology in arterial disease," *Clinical Science*, 71: 137-146 (1986).
Matrai et al., "A Simple Method of Estimating Whole Blood Viscosity at Standardized Hematocrit," *Clinical Hemorheology*, 7: 261-265 (1987).
Nwankwo et al., "Fluid property investigation by impedance characterization of quartz crystal resonators—Part II: Parasitic effects, viscoelastic fluids," *Sensors and Actuators*, 72: 195-202 (1999).
Rosencranz et al., "Clinical Laboratory Measurement of Serum, Plasma and Blood Viscosity," *Am. J. Clin Pathol.*, 125(Suppl. 1): S78-S86 (2006).
Wang et al., "Electrochemical Glucose Biosensors," *Chem. Rev.*, 108: 814-825 (2008).
Ho, "White Blood Cell and Platelet Counts Could Affect Whole Blood Viscosity," *J Chin Med Assoc*, 67: 394-397 (2004).
Shah et al., "Modeling a Piezoelectric TSM Sensor to study Kinetics of Multi-layer Biosensing Structure," *IEEE/EMBS International Summer School on Medical Devices and Biosensors (ISSS-MD)*, pp. 12-16 (2004).
PCT Notification of Transmittal of the International Search Report and the Written Opinion of the International Searching Authority, or the Declaration for International Application No. PCT/US2013/021597, dated Aug. 27, 2013 (18 pages.).
Ram Kumar et al., "Silicon ultrasonic horn actuated microprobes based self-calibrating viscosity sensor," *2010 IEEE 23rd International Conference on Micro Electro Mechanical Systems (MEMS)*, pp. 991-994 (2010).
PCT Invitation to Pay Additional Fees and, Where Applicable, Protest Fee, and Communication Relating to the Results of the Partial International Search for International Application No. PCT/US2013/021597, dated Jun. 13, 2013 (5 pages.).
Japanese Patent Application No. 2014-552385, by Abram Scientific, Inc.: Notice of Reasons for Rejection, dated Oct. 31, 2017, with English translation (10 pages).

\* cited by examiner

METHODS, DEVICES, AND SYSTEMS FOR MEASURING PHYSICAL PROPERTIES OF FLUID

This application is a division of U.S. application Ser. No. 13/742,244, filed on Jan. 15, 2013, entitled, "METHODS, DEVICES, AND SYSTEMS FOR MEASURING PHYSICAL PROPERTIES OF FLUID", which claims the benefit of U.S. Provisional Patent Application No. 61/587,020, filed on Jan. 16, 2012, entitled, "METHODS, DEVICES, AND SYSTEMS FOR MEASURING PHYSICAL PROPERTIES OF FLUID", which is incorporated herein by reference.

The present invention relates to methods, devices, and systems for measuring physical properties of fluid, e.g., viscosity of a fluid sample, viscosity of a bulk phase of a fluid sample, viscosity of a continuous phase of a fluid sample, viscoelasticity of a fluid sample, density of a fluid sample, plasma viscosity of a blood sample, whole blood viscosity of a blood sample, viscoelasticity of a blood sample, a blood clotting time of a blood sample, a hematocrit of a blood sample, and a concentration of anticoagulant in a blood sample.

Whole blood viscosity (WBV), a global measure of the intrinsic resistance of bulk blood to flow in vessels, is determined by the interaction between blood cell rheology, plasma viscosity (PV) and hematocrit, and may be considered a marker of circulatory function. Its major determinants are the volume fraction of red blood cells (Hematocrit or Hct), plasma viscosity (determined mainly by plasma fibrinogen, other biologically reactant globulins, and lipoproteins), red cell deformation (under high flow/shear conditions) and red cell aggregation leading to clotting/coagulation (under low flow/shear conditions) [1, 2]. It has been shown that increasing levels of blood viscosity within the general population may promote cardiovascular events through its potential rheological effects on atherogenesis, thrombogenesis, or ischemia distal to atherothrombotic stenoses or occlusions [1, 3]. Epidemiological studies have associated high blood viscosity with conventional risk factors such as the male gender, cigarette smoking, blood pressure, and plasma lipid/lipoproteins [2, 4]. A study of a random population of 1592 men and women, followed over a mean of 5 years, showed mean blood viscosity, after adjustment for age and sex, was higher in patients experiencing ischemic heart attacks and strokes than those who did not [5]. After correction for diastolic blood pressure, LDL cholesterol and smoking, the link between blood viscosity (and hematocrit-corrected blood viscosity) was significant only for stroke ($p<0.05$). A recent prospective study of 331 middle-aged hypertensive men (followed for an average of 4.8 years) revealed that the top tertile diastolic blood viscosity patients had increased risk of cardiovascular events [6]. Also, there is a strong correlation between the incidence of type-2 diabetes with WBV, and both the prediction of plasma hyperviscosity syndrome and the prognosis of sickle cell disease with plasma viscosity.

Blood is a non-Newtonian fluid, i.e., the viscosity of blood is dependent on the velocity of blood through vessels (more specifically, blood's shear rate). At high velocities of blood, the disc-shaped red blood cells orient in the direction of the flow and the viscosity is lower. For extremely low shear rates red blood cell aggregation may occur, thus increasing viscosity to very high values. It has also been suggested and demonstrated that a minimum shear stress (yield stress, $\tau_y$) is required before the blood will start to flow. To measure the viscosity of a sample, modern viscometers generally measure the rate of fluid flow at a specified force or, conversely, the amount of force required to achieve a predefined rate of flow. It does not matter which method is used for plasma viscosity measurement due to its Newtonian fluid properties. The rate of flow (proportional to shear rate) ideally should be precisely controlled and specified when measuring whole blood viscosity so as to foster standardization of measurement. Viscometers commonly derive the viscosity of a fluid by measuring the force required to achieve the specified shear rate (Wells-Brookfield, cone-plate type viscometer) [7]. Conventional laboratory viscometers are often not conducive for portable and online measurement of viscosity due to their cost, space requirements, and other pre-conditions, e.g., vibration-free mounting. Also, sample taking for such devices often involves manual labor and tends to be time-consuming and error-prone.

Vibration-damping based sensors can be used for fluid property measurement. The vibration based sensors when exposed to a fluid induce an acoustic vibration field in the medium, which results in a viscosity-modified damping or flow that can be measured electronically, optically, etc. When the vibration of the sensors corresponds to a resonance oscillation of the sensor, the damping of the oscillation can be measured using the quality factor of the resonance, the resonance frequency, and/or the resonant motion amplitude, among other variables. Examples of such sensors include microacoustic sensors like quartz thickness shear mode resonators (TSM) [10] and surface acoustic wave (SAW) devices which have been successfully used as alternatives to traditional viscometers [11]. These devices generally measure viscosity at relatively high frequencies and small vibration amplitudes, which can lead to significant disadvantages. Since the penetration depth ($\delta_s = \sqrt{\eta/\rho\pi f}$) of the acoustic field excited by these sensors is small (when high frequencies are used), only a thin film of liquid close to the device is probed. Thus for non-Newtonian fluids or fluids containing discrete components/additives, the results may not be directly comparable to results from conventional viscometers.

In some embodiments, the present invention provides an acoustic vibrating sensor that can generate for relatively greater vibration amplitudes and acoustic field penetration depths in fluids, which in turn can lead to a higher sensitivity and larger breadth of measurement of fluid properties. In some embodiments, the vibrating element is such that at least two acoustic fields corresponding to two different penetration depths can be induced in the fluid medium, and consequently different physical properties of the fluid can be measured using the two acoustic fields. For example, by using two penetration depths that are greater than and smaller than the size of discrete components/additives in the fluid, the viscosity of the continuous phase and the bulk phase (which reflects contribution from discrete components/additives) can be accurately determined in the same sample, without need for separating the discrete components/additives. Also, by varying the vibration mode of the sensor in a device according to some embodiments, the density of the fluid can also be precisely measured, which in turn may be used to quantify the concentration of any discrete components/additives. This sensor could be found useful in a wide variety of fluid property measurement applications, e.g., measurement of properties of foods, beverages, paints, and inks, as well as biological fluids in vivo and in vitro.

In some embodiments, methods and devices according to the invention provide advantages for the measurement of whole blood viscosity, which is highly dependent on the viscosity of its continuous phase, i.e., plasma, and the concentration of discrete components such as red blood cells.

Some embodiments of the invention provide sensors that enable the simultaneous and rapid measurement of whole blood and plasma viscosities on the same blood sample and/or that can be configured to measure the density of blood which can be used to determine the hematocrit, because of the density being linearly related to the hematocrit by the simple relationship $\rho=1.026+0.067\text{Hct}$ gm/cc [12]. Since whole blood viscosity is highly dependent on the plasma viscosity and hematocrit, in order to compare/group the blood viscosity of different individuals it may be advisable to standardize the blood viscosity to a fixed hematocrit (0.45 is generally used). In most of the studies whole blood viscosity was standardized (or corrected) to a standard hematocrit of 45% by the formula of Matrai et al. [8]—

$$\left(\frac{\eta_{WBV-0.45}}{\eta_{plasma}}\right) = \left(\frac{\eta_{WBV-Hct}}{\eta_{plasma}}\right)^{\frac{0.45}{Hct}}$$

where $\eta_{WBV-0.45}$ is the corrected whole blood viscosity, $\eta_{WBV-Hct}$ is the whole blood viscosity at hematocrit Hct, and $\eta_{Plasma}$ is the plasma viscosity. Thus in order to estimate the standardized blood viscosity using this approach, the hematocrit, whole blood viscosity and plasma viscosity of a sample need to be accurately determined. Currently, the measurement of blood and plasma viscosities generally involves time-consuming sample processing viz. centrifugation of red blood cells to separate plasma and measure hematocrit, and measurement of viscosities using bulky instruments by trained professionals. Also, since the blood volumes available from patients are small they must be analyzed quickly, preferably without the addition of anticoagulants. The currently existing methods for clinical diagnosis and in vitro study of blood in laboratories generally involve the addition of anti-coagulants such as EDTA, thus deviating from the true physiological state of blood [9]. In some embodiments, the invention provides the advantage of performing all three measurements viz. whole blood viscosity, plasma viscosity and hematocrit measurement on the same blood sample without requiring pre-processing of the samples, thus serving as a rapid, point-of-care diagnostics tool.

The capability of measuring the physical properties of blood rapidly can allow for monitoring the properties as a function of time, including real-time monitoring of the coagulation of blood. The currently used hemorheological tests for diagnosis and monitoring of diseases include blood coagulation tests such as Prothrombin Time (PT), Partial Thromboplastin Therapy (PTT), Activated Clotting Time (ACT) and Thromboelastogram (TEG).

The above mentioned tests conducted in clinics may require large samples of blood (3-5 ml) and the addition of anti-coagulants, often with long turn-around times of at least 1-2 days. Also, the tests generally do not directly measure the effect of drugs (Warfarin, Coumarin, Heparin etc.) on blood viscosity, i.e., thinning or reducing blood viscosity, but instead measure their second order effect on blood clotting.

The currently existing hand-held point of care units used in home and anticoagulation clinics (Coaguchek™, Hemosense™ etc.), generally follow the pin-prick blood sampling and strip-based collection method as is commonly used by blood-glucose meters, and measure blood coagulation times (PT/INR & PTT). Though these devices are portable and easy to use, they generally do not measure the effect of the anti-coagulation therapy on whole blood viscosity, which could indicate the real-time effectiveness of the drug therapy. A real-time measurement of the physical property of the complex fluid (here, blood viscosity) may help give real-time feedback on the effectiveness and response time of the treatment/therapy in a clinic allowing for tighter control. Also, monitoring viscosity as a function of time can be used in performing multiple coagulation tests on the same blood sample (PT/INR, PTT & ACT). Such a device could in effect be used for measuring blood & plasma viscosities and perform standardized coagulation measurements (including but not limited to PT/INR, PTT, ACT & TEG) for home monitoring as well, thus giving a comprehensive picture of the therapy induced changes to blood.

Thus, there is a current need for low sample volume (e.g., <5 µl, including but not limited to pin-prick blood sampling in a disposable strip), rapid real-time measurement of rheological properties of whole blood and plasma (viscosity and coagulation) in vitro or in vivo. Such an instrument, together with biosensors such as, e.g., glucose measurement for diabetic patients, could serve as an invaluable tool for rapid diagnosis and monitoring of disease and blood function.

Accordingly, in one embodiment, the invention provides a device for measuring, at one or more time points, one or more properties or changes in properties of a fluid sample, the device comprising: a chamber defining an internal volume of the device suitable for receiving and retaining the fluid sample; a plurality of layers, the plurality comprising at least a first layer below the chamber, at least a second layer above the chamber, and a substrate layer between the first and second layers, wherein: the substrate layer is linked to at least one suspended element which is not substantially metallic located within the chamber; the suspended element is linked to the substrate layer by at least two compliant structures located within the chamber; and the suspended element is configured to oscillate upon application of an actuating signal to at least one electrically conductive path, which runs across at least two of the compliant structures and the suspended element.

In another embodiment, the invention provides a device for measuring, at one or more time points, one or more properties or changes in properties of a fluid sample the device comprising: a chamber defining an internal volume of the device suitable for receiving and retaining the fluid sample; a plurality of layers, the plurality comprising at least a first layer below the chamber, at least a second layer above the chamber, and a substrate layer between the first and second layers, wherein: the substrate layer is linked to at least one suspended element located within the chamber; the suspended element is linked to the substrate layer by at least two compliant structures located within the chamber; the suspended element is configured to oscillate upon application of an actuating signal to at least one electrically conductive path, which runs across at least two of the compliant structures and the suspended element; the suspended element and the at least two the compliant structures are configured to have at least a first oscillation frequency and a second oscillation frequency; oscillation at the first oscillation frequency induces a first acoustic field in the fluid sample with a first shear penetration depth smaller than a threshold value, wherein the threshold value ranges from 0.5 microns to 500 microns, and oscillation at the second oscillation frequency induces a second acoustic field in the fluid sample with a second shear penetration depth greater than the threshold value.

In another embodiment, the invention provides A method of measuring one or more properties or changes in properties of a fluid sample using a device according to claim 1, the method comprising: placing the fluid sample in the chamber of the device; oscillating at least one suspended element of the device, wherein the oscillation causes a current or voltage in at least one of the electrically conductive paths of the device; measuring the current or voltage at one or more times; and using one or more of the measurements of the current or voltage to calculate the one or more properties or changes in properties of the fluid sample.

In another embodiment, the invention provides a method of determining one or more properties or changes in properties of a fluid sample at an arbitrary concentration of an analyte present in the fluid sample, the method comprising: placing the fluid sample in a chamber comprising a physical element capable of oscillating in-plane; oscillating the physical element in-plane at a first oscillation frequency, thus inducing a first acoustic field in the fluid sample with a first shear penetration depth smaller than the size of the analyte in the fluid sample; measuring one or more characteristics of the oscillation of the physical element at the first oscillation frequency; oscillating the physical element in-plane at a second oscillation frequency simultaneously or non-simultaneously with the oscillation at the first oscillation frequency, thus inducing a second acoustic field in the fluid sample with a second shear penetration depth greater than the size of the analyte in the fluid sample; measuring one or more characteristics of the oscillation of the physical element at the second oscillation frequency; determining one or more properties of the fluid sample using one or more of the measured oscillation characteristics, determining the actual concentration of the analyte in the fluid sample using one or more of the properties of the fluid sample and optionally one or more of the measured oscillation characteristics; and calculating one or more properties of the fluid sample at an arbitrary concentration of the analyte, wherein the arbitrary concentration of the analyte is different from the actual concentration of the analyte.

In another embodiment, the invention provides a use of a device according to the invention for the determination of at least one of viscosity of a fluid sample, viscosity of a bulk phase of a fluid sample, viscosity of a continuous phase of a fluid sample, viscoelasticity of a fluid sample, density of a fluid sample, plasma viscosity of a blood sample, whole blood viscosity of a blood sample, viscoelasticity of a blood sample, a blood clotting time of a blood sample, a hematocrit of a blood sample, and a concentration of anticoagulant in a blood sample.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

The foregoing aspects and advantages of this invention may become apparent from the following detailed description with reference to the accompanying drawings in which:

FIG. 1(a) shows an arrangement with a suspended element attached to two compliant structure undergoing in-plane oscillations, in accordance with an exemplary embodiment. FIG. 1(b) shows an arrangement with a suspended element attached to four compliant structures undergoing in-plane oscillations, in accordance with a further exemplary embodiment.

FIG. 5(a) shows a graph detailing the results of a single frequency scan of a physical element undergoing in-plane oscillations with air present in the chamber, the frequency scan is of the embodiment presented in FIG. 2 between 4100 Hz and 4550 Hz, while FIG. 5(b) shows a graph detailing the results of a single frequency scan of the same physical element undergoing out-of-plane oscillations with air present in the chamber, the frequency scan is between 400 Hz and 800 Hz.

DETAILED DESCRIPTION OF THE INVENTION

Definitions

Figure 1A:
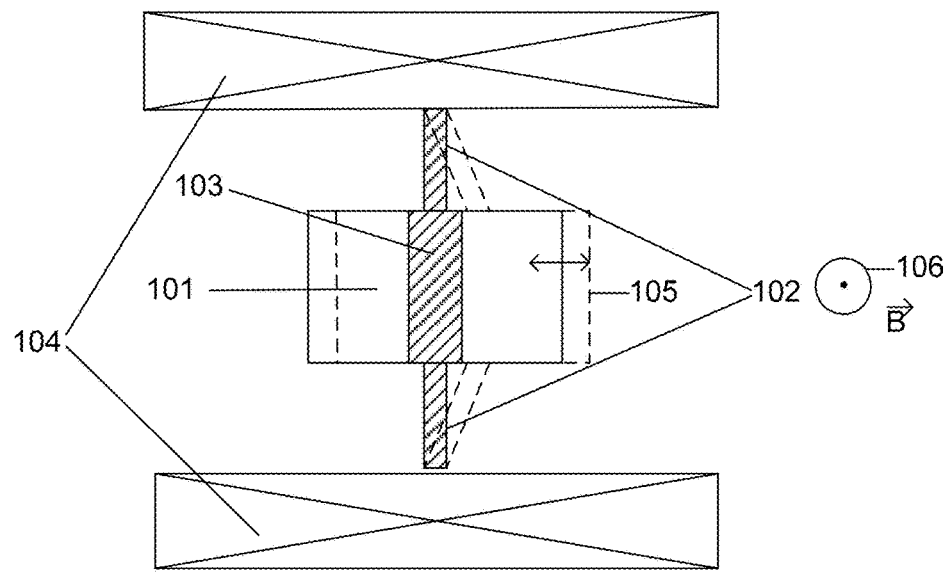
FIGS. 1(a) and 1(b) depict schematically two embodiments of a substrate layer comprising a suspended element and at least 2 compliant structures, which is suitable for measuring the absolute value of and/or changes in the viscosity, viscoelasticity and/or density of a fluid sample independently and/or before, during and after a reaction.

To facilitate the understanding of this invention, a number of terms are defined below. Terms not defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Prothrombin Time (PT) or International Normalized Ratio (INR) test is an important index for the activity of coagulation factors of the extrinsic pathway—it is the coagulation time when tissue thromboplastin (a tissue factor) and calcium ion are added into the plasma specimen to induce coagulation formation. Warfarin and Coumarin are prescribed to slow down the extrinsic pathway and their effectiveness is measured by the PT test.

Partial Thromboplastin Time (PTT) test is an indicator of coagulation factors of the intrinsic pathway, measuring the time whole blood takes to coagulate. PTT is often used as a starting place when investigating the cause of a bleeding or thrombotic episode. The PTT test is used to determine the effectiveness of Heparin therapy prescribed to patients with perturbations in the intrinsic pathway (typically during invasive procedures).

Activated clotting time (ACT) test is used to monitor the effect of high-dose heparin before, during, and shortly after surgeries that require intense anticoagulant administration, such as cardiac bypass surgery, cardiac angioplasty, and dialysis. It is ordered in situations where the partial thromboplastin time (PTT) test is not clinically useful or takes too long.

Thromboelastography (TEG) is a method of testing the efficiency of coagulation of blood. It is especially important in surgery, anesthesiology and trauma-related treatment. A small sample of blood (typically 0.36 ml) is placed into a cuvette (cup) which is rotated gently through 4° 45' (cycle time 6/min) to imitate sluggish venous flow and activate coagulation. When a sensor shaft is inserted into the sample a clot forms between the cup and the sensor. The speed and strength of clot formation is measured in various ways and depends on the activity of the plasmatic coagulation system, platelet function, fibrinolysis and other factors which may be affected by illness, environment and medications.

The quality factor (Q-factor) is a measurement of the "quality" of a resonant oscillating system; it is a measure of the sharpness of the oscillation's resonance or frequency selectivity of a resonant vibratory system, measured in a range of frequencies in the vicinity of the resonance oscillation frequency. The Q-factor can be measured by monitoring the amplitude of oscillation as a function of frequency in the vicinity of the resonance frequency. The Q-factor can be defined in multiple ways; a common definition is the ratio of the resonance frequency to the width of the peak. The width of the resonance peak can be determined, for example, as the distance between the two frequencies above and below the resonance frequency where the amplitude of oscillation falls to half the magnitude of the amplitude at the resonance frequency, which is generally known as the Full Width Half Max (FWHM).

Shear penetration depth ($\delta_s$) is calculated as $$\delta_s = \sqrt{\eta/\rho\pi f}$$

where f is the oscillation frequency, $\eta$ is the viscosity of the fluid sample and $\rho$ is the density of the fluid sample.

Determination of properties of a fluid, including but not limited viscosity and density, can be achieved by determining the oscillation characteristics of a physical element. The oscillation may correspond to one of the natural or fundamental frequencies of resonance or oscillation of the physical element. The principle of resonance may be further defined with respect to the function of a tuning fork. When a tuning fork is excited by striking it against a surface or an object, its resonating beams or prongs resonate at a certain frequency known as the fundamental frequency. The fundamental frequency of the prongs is dependent on the physical characteristics of the prongs such as the length and cross-sectional area of the prong, as well as the material from which the fork is made. More generally, the fundamental frequencies of resonance or oscillation of any physical element are dependent on the geometric shape and material properties of the same.

Electromagnetism has been used for inducing and monitoring motion as part of a variety of applications, for example, in rotors as part of motor assemblies. A possible electromagnetic mechanism of actuation involves applying an electrical current in the presence of a magnetic field resulting in a motion in the current carrying substrate as a result of the Lorentz force experienced by the conductor.

Lorentz force $F_L$ is defined as the force experienced by a charge q moving with a velocity v in the presence of an electric field E and a magnetic field B given by $F_L=q[E+(v \times B)]$. Alternatively, the motion in a moving body with a conductive path through it can be detected by electromagnetic induction. Electromagnetic induction is the production of an electric current or voltage across a conductor moving in the presence of a magnetic field. Thus, using the principles of electromagnetism, motion can be both induced and monitored precisely. Alternatively, actuation methods such as piezoelectric, capacitive, electromagnetic, and thermal can be used to induce and monitor motion. Motion can also be monitored optically.

In some embodiments of the present invention, a device is provided in which the oscillation of a physical element (formed on or part of a substrate layer), comprising a suspended element suspended by at least two compliant structures attached to the substrate, is configured for monitoring the physical characteristics of a fluid. The physical element is provided with at least one conductive path running through it, and the suspended element may have a planar, flat shape. An example of a planar, flat shape can be a rectangular shape with length and width in the range of 1 to 10 mm, and thickness less than $\frac{1}{5}^{th}$ the length or width, with the flatness of the element defined by a surface roughness of less than $\frac{1}{5}^{th}$ the length or width. The compliant structures may have a straight or meandering shape (compare FIGS. 1 and 2). When an actuating signal by way of a current is passed through the physical element in the presence of a magnetic field with flux lines intersecting the physical element, oscillation is induced in the physical element. At a constant magnetic field, when an electric field via a time-varying current is applied/injected through the physical element, oscillation is induced in the physical element. Alternatively, applying a constant electric field through the physical element in the presence of a time-varying magnetic field can also be used to induce oscillation in the physical element. Also, the relative direction of the electric and magnetic fields can target specific oscillations and control the oscillation characteristics (such as amplitude, frequency, etc.) in the physical element. The oscillation is monitored by measuring the detection signal i.e. voltage or current induced by electromagnetic induction, in the at least one conductive path through the physical element, in a range of frequencies in the vicinity of the oscillation frequency. In some embodiments of the invention, the actuation and detection signal are applied and measured across the same or independent conductive paths through the physical element. Alternatively, other methods including but not limited to optical, piezoelectric, thermal, etc. can be used to monitor the oscillation.

The oscillation induced in the physical element can be at either a resonance or non-resonance frequency of the physical element. In some embodiments of the invention, when the frequency of the time-varying actuating signal corresponds to one or more of the natural or fundamental frequencies of resonance of the physical element, the corresponding mode(s) of oscillation is/are induced in the physical element. The resonance oscillation characteristics can vary depending on the physical dimensional structure and material of the physical element i.e. the suspended element and compliant structures, which can target specific frequencies of oscillation.

For example, the suspended element can be flat and rectangular. Given the length l and width w of the rectangular element, one can design two specific frequencies of resonance of the physical element along the length and width directions, respectively, and the magnitude of the resonance frequencies can be controlled by the corresponding lengths l and w. Alternatively, the geometry and structure of the compliant structures connected to the suspended element can also be configured to tailor the resonance oscillation frequencies. In some embodiments of the invention, the resonance frequencies of oscillation can correspond to in-plane and out-plane modes of oscillation of the physical element. In some embodiments of the invention, the resonance characteristics of the induced oscillation in the physical element can be computed by monitoring the induced detection signal in a range of frequencies in the vicinity of the resonance oscillation frequency. The measureable or quantifiable oscillation characteristics of the physical element include without limitation oscillation amplitude, phase, frequency and quality factor. In some embodiments of the invention, the actuation signal may correspond to a first resonance oscillation that couples to a second resonance oscillation, and results in both modes of oscillation being induced in the physical element. In this case, the detection signal can be measured in the vicinity of either or both of the induced oscillation frequencies.

In another embodiment of the invention, the oscillation of the physical element can be induced by coupling, interfacing or contacting the substrate where the physical element is located with a vibration inducing actuator which uses one excitation field or a combination of excitation fields chosen from (i) piezoelectricity-based mechanical, (ii) capacitive, (iii) electromagnetic, and (iv) thermal excitation fields. In some embodiments of the invention the physical element is provided with at least one conductive path running through it which may comprise elements with limited conductivity such as thermal resistors, piezoelectric resistors, etc. For example, a piezoelectric quartz crystal (PZT) oscillator can be physically affixed to the substrate, and the PZT oscillator can be driven to induce oscillations in the physical element at a particular oscillation frequency. When the PZT oscillator is driven at a frequency corresponding to one of the natural or fundamental frequencies of resonance of the physical element the corresponding mode of oscillation is excited. The geometric shape and material properties of the physical element, which may comprise a planar flat element suspended by compliant structures, can be configured for the natural or fundamental frequency/frequencies of resonance of the physical element to be a specific value or within a given range of frequencies such as 1 Hz to 1 MHz. The PZT when actuated at these above mentioned frequencies induces resonance oscillations in the physical element.

Another embodiment involves applying capacitive fields between the physical element and one or more isolated, stationary electrode (located at a finite distance from the substrate linked to the physical element) to induce oscillations. The capacitive fields can be set up by applying a time-varying voltage signal between the conductive path running through the physical element and the stationary electrodes. Resonance oscillations in the physical element can be induced by applying a time-varying voltage at the natural or fundamental frequencies of the physical element.

In yet another embodiment, thermal resistors are provided as part of the conductive path running through the physical element. Oscillations in the physical element corresponding to its natural or fundamental frequencies of resonance can be induced by heating the resistors by passing current through the conductive path running through the physical element. By applying a time-varying current signal, steady-state or transient oscillations can be induced in the physical element.

In another embodiment of the invention, the oscillation induced in the physical element is detected by one detection field or a combination of detection fields chosen from (i) piezoelectricity-based electrical, (ii) capacitive, (iii) electromagnetic, (iv) thermal and (v) optical detection fields arising due to the oscillation. For example, when a piezoelectric quartz crystal (PZT) oscillator affixed to the substrate is used to induce oscillations in the physical element, the oscillation characteristics can be monitored by measuring the PZT's electrical input characteristics in a frequency range in the vicinity of the oscillation frequency excited in the physical element.

Alternatively, one or more piezoelectric resistors can be provided as part of the conductive path running through the physical element, which exhibit a change in resistance due to the oscillation of the physical element. The oscillation can be monitored by incorporating the piezoelectric resistors as part of a Wheatstone bridge circuit and measuring the bridge voltage in a frequency range in the vicinity of the oscillation frequency excited in the physical element.

In yet another alternative, one or more thermal resistors are provided as part of the conductive path running through the physical element that can measure the change temperature due to the oscillation of the physical element. The thermal resistors can be made of pyroelectric materials which have the ability to induce a voltage with a change in temperature. The oscillations in the physical element can be monitored by measuring the change in voltage across the resistors in a frequency range in the vicinity of the oscillation frequency excited in the physical element.

In yet another alternative, an optical sensor module is used to direct an optical signal onto the physical element and monitor the reflected optical signal using a photodetector. The oscillations in the physical element can be monitored by measuring the photodetector output signal in the vicinity of the oscillation frequency excited in the physical element. Alternatively, a photodetector module can be incorporated on the physical element as part of the conductive path running through it. When an optical signal is directed onto the photodetector, the oscillation in the physical element can be monitored by measuring the change in the photodetector output in a frequency range in the vicinity of the oscillation frequency excited in the physical element.

When a fluid sample is present in the chamber with the physical element, the effect(s) (e.g., damping) on the oscillations in the physical element can be used to determine one or more physical characteristics of the fluid such as viscosity and density. In some embodiments of the invention, the oscillation induced in the physical element can be at a non-resonance frequency. The measureable or quantifiable oscillation characteristics of the physical element include without limitation oscillation amplitude, phase, frequency and quality factor. In all resonating devices, the quality factor is affected by the surroundings; the quality factor of a resonant system changes according to the viscosity, viscoelasticity and density of the media in which it oscillates. The amplitude of the oscillating element is proportional to the fluid viscosity; in a low viscosity fluid, the element will oscillate with much higher amplitude over a narrow frequency range near the natural or fundamental frequency, compared to when in a high viscosity fluid. Introduction of a fluid sample in the vicinity of the physical element causes damping in its oscillation characteristics, and changes in amplitude, frequency and/or quality factor are indicative of the viscosity, viscoelasticity and density of the fluid. In some embodiments of the invention, the conductive path through the physical element comprises one or more heating elements, including but not limited to for example, one or more resistive track heaters, to control the temperature of the fluid medium in the chamber, and/or one or more sensing elements, to monitor the temperature of the fluid medium in the chamber.

In some embodiments of the invention, when the physical element is surrounded by a biological fluid which can undergo a reaction leading to coagulation, the resonating element is further dampened by the increasing viscosity of the fluid sample as it coagulates. This damping effect can be measured periodically (i.e., at two or more time points) to determine the coagulation of the body fluid as a function of time. In some embodiments of the invention, the biological fluid comprises blood or plasma. In some embodiments, the coagulation is initiated by physical contact with negatively charged substrates or by the addition of blood coagulation-inducing compounds, for example, thromboplastin, and the time to formation of the blood clot can be accurately determined as part of blood tests such as Prothrombin Time (PT), Partial Thromboplastin Time (PTT), Activating Coagulation Time (ACT), etc.

In another embodiment of the invention, one or more physical elements are present in a chamber, defining an internal volume which is suitable for receiving and retaining a fluid sample, and the one or more suspended elements are configured to oscillate upon application of an actuating signal.

In some embodiments of the invention, the internal volume of the chamber is configured to receive and hold the fluid sample in place before fluid property measurement is performed. The chamber is formed by a plurality of layers such that there exists at least one layer above (upper substrate) and one layer below (lower substrate) the chamber, such that the substrate layer comprising the physical element is in between the layers. The substrate layer may generally be parallel to the layers above and below the chamber, except to the extent of out-of-plane oscillations of the physical element of the substrate layer during which the physical element (including the suspended element and/or compliant structures) is deformed from a parallel configuration.

As discussed earlier, the fluid characteristics can be determined from oscillation characteristics of the physical element. Alternatively, the entire structure composed of the physical element and chamber formed by the upper and lower substrates, can be oscillated at a corresponding resonance or non-resonance frequency to determine the fluid characteristics such as the fluid density. The additional mass of the fluid once introduced in the chamber dampens the oscillation of the entire structure and subsequently shows reduction in measureable oscillation characteristics such as oscillation amplitude, frequency and Q-factor.

In-Plane Vibration

One method of measuring viscosity of a fluid involves trapping the fluid between a fixed and moveable parallel plates or planar structures, and monitoring the drag experienced by the moveable planar structure when it is moved in its own plane at a constant velocity relative to the fixed planar structure. The fluid experiences a true shear stress resulting in a shear strain on the fluid, and the fluid viscosity is computed as determined by the ratio of the stress applied to the strain experienced by the fluid.

Miniaturized microacoustic sensors like quartz thickness shear mode resonators (TSM) and surface acoustic wave (SAW) devices have been successfully used as alternatives to traditional viscometers, but these devices measure viscosity at relatively high frequencies and small vibration amplitudes. Since the penetration depth ($\delta_s = \sqrt{\eta/\rho \pi f}$) of the shear waves excited by these sensors are small (due to high frequencies), only a thin film of liquid close to the device is probed. In addition due to the small penetration depth these sensors are unable to detect the presence and effect of particles (size>$\delta_s$) in complex or non-Newtonian fluids, and can only measure the viscosity of the continuous phase of the fluid. Finally, the smaller vibration amplitude in these sensors results in lower measurement sensitivity.

In devices and methods according to the present invention, the physical element can be configured so that the suspended element has at least one natural or fundamental frequency of vibration corresponding to an in-plane oscillation. When a fluid sample is introduced and confined in the chamber containing the physical element, the oscillation induced in the physical element applies a true shear stress to the fluid trapped between the physical element and the upper & lower layers. By measuring vibration characteristics of the physical element, which can be further translated into the shear rate and shear stress experienced by the fluid, the fluid viscosity can be determined. In some embodiments of the invention, the physical element's in-plane oscillation can be tailored to be sensitive to the fluid density and hence, the fluid density can be determined from the damping of oscillation characteristics. This device and methodology offer high-accuracy measurement of the absolute and instantaneous value of the fluid viscosity in a small fluid sample.

In one embodiment of the invention, based on the geometric design, structure and material properties of the physical element the oscillation frequency can be relatively low, such as in the range of a few Kilo-Hertz or less (e.g., less than or equal to 5, 4, 3, 2, or 1 kHz), resulting in a relatively large shear penetration depth into the fluid under concern. Also, higher oscillation amplitudes can be achieved resulting in higher sensitivity to fluid viscosity. In another embodiment of the invention, the physical element can have at least two in-plane oscillation modes, one with a low frequency (see above) and the other with high frequency (e.g., 10 KHz or more), thus having two distinct oscillation modes with large and small shear penetration depths respectively. In a fluid comprising discrete components/additives, including non-Newtonian fluids, the oscillation corresponding to a shear penetration depth smaller than the size of the discrete components/additives can be used to determine the fluid viscosity corresponding to the continuous phase, and shear penetration depth larger than the size of the discrete components/additives can be used to determine the bulk viscosity of the fluid. In some embodiments of the invention, the size of the discrete components/additives can be a number in the range of 0.5 to 500 µm. "Size" may refer to the hydrodynamic diameter or the largest physical dimension measured along standard Cartesian coordinates. These two in-plane oscillation modes can be induced in the physical element simultaneously or in sequence, thus enabling the measurement of the viscosity of the continuous and bulk phases of complex or non-Newtonian fluids. In some embodiments of the invention, the amplitude of vibration induced in the physical element can be controlled by increasing the amplitude of actuation subsequently controlling the shear rate ($\dot{\gamma}$) applied to the fluid. In some embodiments of the invention, where electromagnetic actuation is employed the amplitude of vibration can be changed by changing the magnitude of current through the conductive path and/or the magnetic field applied. Thus fluid viscosity at varying shear rates can be determined for complex or non-Newtonian fluids.

In some embodiments, the device can be configured so that the physical element oscillation induces a first acoustic field in the fluid sample with a first shear penetration depth smaller than a threshold value, wherein the threshold value ranges from 0.5 microns to 500 microns, and oscillation at the second oscillation frequency induces a second acoustic field in the fluid sample with a second shear penetration depth greater than the threshold value. In some embodiments, the first and second shear penetration depths differ by at least a minimum amount, which may be a value greater than or equal to 0.5, 1, 2, 3, 4, 5, or 10 microns, or a value ranging from 0.5 to 1, 1 to 2, 2 to 3, 3 to 4, 4 to 5, or 5 to 10 microns.

In some embodiments of the invention, when a biological fluid such as blood is introduced in the chamber, the two in-plane oscillation modes can have penetration depths greater or smaller than the average size of the red blood cells which form the discrete component in the sample. In some embodiments of the invention, the two in-plane oscillation modes can have penetration depths greater or smaller than 5 µm, which corresponds to a lower limit of the size of red blood cells. In some embodiments of the invention, the two in-plane oscillation modes can have penetration depths greater or smaller than 10 µm, which corresponds to an upper limit of the size of red blood cells. As discussed above, the two in-plane oscillation modes can be used to measure the viscosity of the plasma (continuous phase) and whole blood (bulk phase) of the blood sample simultaneously or in sequence. In some embodiments of the invention, when a body fluid such as blood is introduced in the chamber, the two in-plane oscillation modes can have penetration depths greater or smaller than the average size of platelets which form the discrete component in the sample. In some embodiments of the invention, the two in-plane oscillation modes can have penetration depths greater or smaller than 2 µm, which corresponds to a lower limit of the size of platelets. In some embodiments of the invention, the two in-plane oscillation modes can have penetration depths greater or smaller than 0.5 µm, which corresponds to a size of some macromolecules or macromolecular assemblies, where the size is defined by the hydrodynamic diameter of the molecule.

The chamber of devices according to the invention defines an internal volume which is suitable for receiving and retaining a fluid sample, and also accommodates at least one physical element in a manner which allows for the motion or oscillation of the suspended element and attached compliant structures. The motion or oscillation can occur in an unimpeded manner, i.e., occupying any of the range of space traversed during the oscillation does not result in collision or contact of the physical element with other solid material. To be clear, "unimpeded" does not mean "without any resistance at all"; fluid, when present, provides a degree of resistance to or damping of to oscillation, and the compliant structures may provide a restoring force when the suspended element is displaced from resting position, and the presence of resistance from fluid, restoring force from the compliant structures, and the like are entirely consistent with "unimpeded" motion or oscillation as used herein. The chamber is defined by means of upper and lower layers positioned above and below the substrate layer, which comprises the physical element enclosed inside the chamber; the substrate layer may be formed, patterned, or otherwise assembled or constructed to comprise the physical element. In some embodiments of the invention, the substrate is affixed to the upper and lower substrates by means of intermediary layers in all areas except for the physical element enclosed inside the chamber, thus effectively restricting motion of the substrate to the physical element alone. In some embodiments of the invention, the chamber can include multiple physical elements in the same substrate or in multiple substrates as part of the plurality of layers in the device.

In another embodiment of the invention, when oscillation is induced in the physical element a shear-wave field is induced in the fluid retained in the chamber. The device can be configured such that the distance between at least one of the upper and lower substrate layers and the physical element (D) has a standing shear-wave field induced in the fluid medium between the upper and/or lower substrates and the suspended element during oscillation. In order to have a consistent and reliable standing shear-wave field induced, the distance D can be smaller than or equal to the shear penetration depth ($\delta_s = \sqrt{\eta/\rho\pi f}$). For example, if the fluid medium is water with density of 1 gm/cc and viscosity of 1 cP and a oscillation frequency of 1 KHz, the distance D should be smaller than or equal to $\delta_s = 17.84$ µm. The lower the ratio of the distance D to the shear wavelength ($\lambda_s$) of the field induced in the medium surrounding the physical element, the higher is the consistency and uniformity of the acoustic field set up in the fluid medium, where $\lambda_s = 2\pi \delta_s/\sqrt{2}$ cos ($\delta_l/2$) where $\delta_s$ is the shear penetration depth ($\delta_s = \sqrt{\eta/\rho\pi f}$) and $\delta_l$ is the loss-tangent angle of the fluid medium.

The distance D is adjustable or permanently fixed depending on the properties of the surrounding medium. In some embodiments of the invention, the distance D can be adjusted by means of intermediate layers between the substrate comprising the physical element and the upper and/or lower substrates. The intermediate layers can be composed of flexible materials such as foam, polymeric substrates, etc., such that the intermediate layer thickness can be varied by applying compression to the device in the thickness direction. The compression pressure can be performed offline before measurement depending on the fluid sample, or in real-time with the fluid under concern introduced into the device and monitoring the standing shear-wave field induced in the fluid. In some embodiments of the invention, the distance D can be adjusted by physically moving the upper & lower substrates closer to or farther away from the physical element by an automated assembly, followed by filling of the region around the physical element between the substrate containing the physical element and the upper & lower substrates in order to form the chamber. The filling material can be one that can flow and change state from a fluid to solid including but not limited to epoxy, etc. In some embodiments of the invention, the acoustic field setup in the fluid trapped between the physical element and the chamber walls can be used to not only determine the viscosity of the fluid but also its viscoelastic properties. Also, the presence of the fixed chamber walls close to the oscillating physical element offers additional benefits for high accuracy monitoring of the change in physical properties of the fluid as a function of time during gel formation.

In some embodiments of the invention, when a biological fluid such as blood is introduced in the chamber and undergoes a coagulation reaction, the blood clot formed between the physical element and the chamber walls can be used to compute the viscoelastic properties of the blood clot. In some embodiments of the invention, the viscoelastic properties of blood undergoing coagulation can be monitored as a function of time and blood tests, e.g., a thromboelastogram (TEG), can be performed.

Out-of-Plane Vibration

In another embodiment of the invention, the suspended element can have at least one natural or fundamental frequency of vibration corresponding to an out-of-plane oscillation. When a fluid sample is introduced and confined in a chamber containing the physical element, the oscillation characteristics are damped. The density of the fluid can be determined by monitoring the oscillation characteristics such as oscillation amplitude, phase, frequency and quality factor. Frequency and other characteristics may be measured as a change in oscillation frequency upon addition of the fluid sample to the chamber. In addition, the physical element's out-of-plane oscillation can be tailored to be sensitive to the fluid density and hence, the fluid density can be determined from the damping of oscillation characteristics. In some embodiments of the invention, the fluid density measured can be used to identify the concentration of at least one discrete component/additive in a fluid. The discrete components/additives can be, for example, macromolecules, macromolecular complexes (e.g., cytoskeletal filaments), red blood cells, platelets, particulates or solid-phase objects. In some embodiments of the invention, the physical element oscillation can be configured for measurement of the density of the continuous phase and bulk phase of the fluid independently using the same or different resonance oscillation mode of the physical element.

In another embodiment of the invention, the physical element can enable the measurement of the fluid's continuous phase viscosity, bulk viscosity and density. In some embodiments of the invention, a standardized measure of bulk viscosity of a fluid can be determined as a function of one or more of viscosity of continuous phase, bulk phase, fluid density and concentration of discrete component/additive (if any). Further, the static or dynamic viscoelastic properties of a fluid as a function of time can be determined from the measured (or standardized-measures) viscosities of the fluid at different applied shear rates using various theoretical or empirical models. For example, from the bulk viscosity measured at varying shear rates can be used with Casson's model given by, $\eta = (\sqrt{\tau_y} + \sqrt{k\dot{\gamma}})/\dot{\gamma}$ where $\tau_y$ is the yield stress of the fluid, $\dot{\gamma}$ is the shear rate applied to fluid and k is a constant, to determine a value for $\tau_y$ and k by statistical methods such as regression analysis.

In another embodiment of the invention, where the fluid under concern is blood introduced into the chamber, the physical element can be used to measure the plasma viscosity ($\eta_{plasma}$, continuous phase), whole blood viscosity ($\eta_{WBV}$, bulk phase) and blood density when exposed to a blood sample. The blood density measured can be used to identify the concentration of red blood cells or hematocrit (Hct) in the sample. Since whole blood viscosity is highly dependent on the plasma viscosity and hematocrit, in order to identify the normalcy or abnormality of blood viscosity of different individuals the blood viscosity needs to be standardized or corrected to a fixed hematocrit (0.45 is generally used). The formula for the standardized or corrected whole blood viscosity at a fixed hematocrit of 0.45 is given by—

$$\left(\frac{\eta_{WBV-0.45}}{\eta_{plasma}}\right) = \left(\frac{\eta_{WBV-Hct}}{\eta_{plasma}}\right)^{\frac{0.45}{Hct}}$$

where $\eta_{WBV-0.45}$ is the standardized or corrected whole blood viscosity at a hematocrit of 0.45, $\eta_{WBV-Hct}$ is the whole blood viscosity at hematocrit Hct, and $\eta_{plasma}$ is the plasma viscosity.

In another embodiment of the invention, the chamber along with the substrate comprising the physical element can be incorporated in a disposable test strip. The chamber is so assembled to have the one or more physical elements in the substrate layer suspended inside the chamber, while another part of the substrate layer is affixed to upper and lower substrates above and below the chamber, as part of a plurality of layers stacked to form the test strip. Further, the chamber can be composed of a plurality of layers patterned/formed in order to have its walls positioned closely together to form a capillary. The materials chosen to create the surfaces of the chamber can be selected to provide a low surface tension and/or contact angle (e.g., less than or equal to 45 degrees) which allows the chamber to fill by a capillary action. These materials are selected as they enhance liquid filling without interfering with the reaction. Examples of such materials will be well known to the person skilled in the art. In some embodiments of the invention, the upper and lower substrate layers of the chamber can comprise a plurality of components, including but not limited to electrically conductive paths to perform electrochemical analysis and/or to detect the presence of an analyte in the fluid and/or the fluid itself in the chamber. In some embodiments of the invention, the electrically conductive paths can be used to perform electrochemical detection of sugar levels in the blood sample introduced into the chamber [13]. In some embodiments of the invention, the upper and lower substrate layers can further comprise electrically conductive paths which contain one or more heating elements, such as resistive track heaters, and/or one or more temperature sensors, to control and monitor the temperature of said chamber, respectively.

In some embodiments, a fluid sample may be introduced into the chamber wherein the fluid sample begins undergoing a chemical reaction soon after its addition. For example, the chamber may contain an agent that reacts with the sample once it is present, or an agent can be added to the sample once it is present, or one or more of the surfaces of the chamber may promote or catalyze a reaction in the fluid sample. When a fluid is introduced and confined to the chamber housed inside the test strip, the oscillation characteristics (amplitude, phase, frequency, Q-factor, etc.) of the physical element will generally stabilize momentarily, before further changes take place due to the chemical reaction, allowing for rapid determination of physical characteristics of the fluid. The fast response time of the sensor can allow for the accurate identification of the time at which the fluid sample was introduced to the chamber.

The substrate layer comprising the physical element can be made of any suitable inert material and may be selected from amongst others: polymers such as polyester (PET), plastics, etc. The substrate layer can be fabricated using mass manufacturing methods including but not limited to roll-to-roll continuous flow manufacturing. The physical elements can be formed or patterned by etching, laser treatment or by mechanical punching of the substrate layer. The electrically conductive paths through the physical elements can be made by means of patterned conductive paths on the substrate layer that form circuits such as in the case of printed circuit boards. The conductive circuits can be of any suitable conductive material and may be selected from, but not limited to conductive polymers, gold, platinum, copper or silver. The conductive paths can be patterned by several methods such as laser ablation, or by screen printing. Further, the conductive paths can be insulated from the fluid by deposition of insulating layers on the conductive paths or, have the conductive layer embedded within the substrate with the physical element.

In some embodiments of the invention, the conductive paths can be exposed to the fluid allowing for electrochemical analysis and/or detection of the presence of an analyte in the fluid and/or the fluid itself in the chamber. In some embodiments of the invention, the conductive paths can be used to perform electrochemical detection of sugar levels in a blood sample introduced into the chamber. The conductive paths would serve to form a closed electrical path through the physical element. In some embodiments of the invention, the substrate comprising the physical element can be made of a substantially metallic material also serving the additional functional purpose of an electrically conductive path through the physical element.

In other embodiments, the suspended element is not substantially metallic. For example, the metal content of the suspended element may be less than 50%, 40%, 30%, 20%, 10%, 5%, or 1% by weight. Configurations of the device in which the suspended element is not substantially metallic can provide beneficial properties. For example, the substrate can be made of polyester and the conductive paths can be formed by printing conductive ink onto the polyester substrate. Use of a suspended element which is not substantially metallic makes it possible to control the geometry of the polyester substrate and the conductive paths independently, consequently enabling greater control over the oscillation characteristics of the suspended element than if the element were substantially metallic. Additionally, polyester, being flexible, is compatible with high-volume roll-to-roll continuous flow manufacturing processes, which can be beneficial to the cost-effective manufacturing of the substrate, e.g., as part of a disposable test strip.

In some embodiments of the invention, the substrate layer on which the physical element is disposed can be patterned by laser cutting a sheet of polyester, onto which the conductive path is printed in a specific pattern to provide conductivity through the physical element. Conductive inks such as silver-ink, Palladium-ink, etc. can be used for printing the conductive path on the substrate layer.

In certain embodiments, a series of edge connectors on the disposable strip could be provided to allow direct contact or connection between a test meter and the physical elements. An additional purpose of the conductive circuit would be to activate the device in readiness to receive a fluid sample, by means of bridging contacts provided by the edge connectors. Alternatively, the physical elements could be excited and/or monitored by non-contact means such as acoustic wave amplitude reflection, light beams or radio frequency. The separate layers of the test strip could be aligned such that no further trimming or adjustment to their size and/or outer peripheral surface would be necessary. However, a plurality of devices could be produced and trimmed to the desired size and shape of the disposable test strip.

In another embodiment of the invention, the fluid under concern is a biological fluid, in particular blood. The chamber can be provided with a reagent comprising at least one blood clotting agent in an amount suitable to induce coagulation of a blood sample in the chamber. In some embodiments of the invention, the reagent is present in dry form in the chamber. The reagent can be added to the chamber before or after completion of assembly of the strip. Further, the reagent can be provided on the physical element of the substrate layer and housed inside the chamber. In some embodiments of the invention, the reagent is added to the chamber prior to or after the introduction of blood. In some embodiments of the invention, the reagent is comprised of one or a combination of anticoagulants (such as Heparin, Warfarin, etc.), viscosity-changing molecules (such as Dextran) and Coagulation factor molecules that can induce coagulation. Generally, Coagulation factor molecules include naturally occurring or synthesized compounds that either promote or inhibit blood coagulation including but not limited to Factor I, II, III, IV, V, VI, VII, VIII, IX, X, XI, XII, XIII, von Willebrand factor, prekallikrein, high-molecular-weight kininogen, fibronectin, antithrombin III, heparin cofactor II, protein C, protein S, protein Z, protein Z-related protease inhibitor, plasminogen, alpha 2-antiplasmin, tissue plasminogen activator (tPA), urokinase, plasminogen activator inhibitor-1 (PAI1), plasminogen activator inhibitor-2 (PAI2) and cancer procoagulant. Generally, "viscosity-changing molecules" include compounds that alter the viscosity of blood by at least 0.001 cP upon introduction into blood of the amount actually added to the blood or present in the chamber. In other embodiments, the above mentioned reagents can be present in the fluid as it is introduced into the chamber and need not necessarily be present in the device as it stands. For example, a reagent could be present in a blood sample as a result of having been administered to the individual who supplied the blood. In another embodiment, the device comprises multiple chambers in which the reagent is provided, accommodating at least one substrate with one or more physical elements in each chamber. Further, the same blood sample can be directed and split into multiple microfluidic paths leading to the different chambers in the device. Thus, blood coagulation can be induced and monitored at discrete regions of the device in the same blood sample.

In some embodiments of the invention, when a biological fluid such as blood is introduced in the chamber, two in-plane oscillation modes can have penetration depths greater or smaller than the average size of red blood cells which form a discrete component in the sample. In some embodiments of the invention, the two in-plane oscillation modes can have penetration depths greater or smaller than 5 µm, which corresponds to an approximate lower limit of the size of red blood cells. As discussed above, the two in-plane oscillation modes can be used to measure the viscosity of the plasma (continuous phase) and whole blood (bulk phase) of the blood sample simultaneously or in sequence. In some embodiments of the invention, when a biological fluid such as blood is introduced in the chamber, the two in-plane oscillation modes can have penetration depths greater or smaller than the average size of platelets which form a discrete component in the sample. In some embodiments of the invention, the two in-plane oscillation modes can have penetration depths greater or smaller than 2 µm, which corresponds to a lower limit of the size of platelets. In some embodiments of the invention, the two in-plane oscillation modes can have penetration depths greater or smaller than 0.5 µm, which corresponds to the approximate size of some macromolecules and/or macromolecular complexes. As discussed earlier, the two penetration depths may differ by at least a minimum amount or by an amount in a given range.

In another embodiment of the invention, where the fluid under concern is blood introduced into the chamber, the physical element is configured to measure the plasma viscosity ($\eta_{plasma}$, continuous phase), whole blood viscosity ($\eta_{WBV}$, bulk phase) and blood density when exposed to a blood sample. The blood density measured can be used to identify the concentration of red blood cells or hematocrit (Hct) in the sample. Since whole blood viscosity is highly dependent on the plasma viscosity and hematocrit, in order to identify the normalcy and abnormality of blood viscosity of different individuals the blood viscosity needs to be standardized or corrected to a fixed hematocrit (0.45 is generally used).

In some embodiments of the invention, the biological fluid comprises of blood or plasma and coagulation can be initiated by physical contact to negatively charged substrates or the addition of blood coagulation-inducing compounds including but not limited to thromboplastin. Thus, a blood coagulation-inducing compound such as thromboplastin may be present in a device according to the invention, including before addition of blood or plasma, and used in methods according to the invention. Alternatively, the blood coagulation-inducing compound such as thromboplastin may be added to blood or plasma present in the chamber. The plasma, whole blood viscosity and/or density of the sample can be monitored before, during and/or after the coagulation reaction. Further, the time to formation of a blood clot can be determined as part of blood tests including but not limited to Prothrombin Time (PT), Partial Thromboplastin Time (PTT), Activating Coagulation Time (ACT), etc. In some embodiments of the invention, when a biological fluid such as blood is introduced in the chamber and undergoes a coagulation reaction, the blood clot formed between the physical element and the chamber walls can be used to measure the viscoelastic properties of the blood clot. In some embodiments of the invention, the viscoelastic properties of blood undergoing coagulation can be monitored as a function of time and blood tests such as a thromboelastogram (TEG) can be performed. In some embodiments of the invention, the hematocrit computed in the blood sample by way of the measured blood density can be used to calibrate the above mentioned blood coagulation tests (PT, PTT, ACT, TEG, etc.) performed.

Monitoring or reading of a device according to the invention in order to provide an automated means for determining the viscosity, viscoelasticity and/or density of a fluid sample can be provided by the use of a machine, such as a metering device, which can interact with the sensor device of the invention in a manner which allows for the meter to determine the results of the sample testing. In some embodiments of the invention, the metering device comprises one or more of the following: processor, bus, input interface such as keypad or data port, input interface such as a resistive or capacitive touch-screen display, output interface such as display screen, output interface such as a data port, wireless connectivity for input and/or output interface, power supply such as battery or power cord or power receptacle, strip connector interface for providing conductivity, etc. In some embodiments of the invention, where the sensor device is connected to, or engaged with a meter, this provides an automated means for determining the physical characteristics of a fluid including but not limited to viscosity, viscoelasticity and/or density. For example, where the meter is connected to the sensor device, the meter could be releasably/temporarily engaged with the test strip and would have the ability to output the test results, typically by means of a visual display or readout. In addition, where the meter processes the data received from the sensor device, the meter may process this information and apply correction factors which would take into account any batch to batch variability associated with the disposable test strip manufacture.

In some embodiments of the invention, the meter may include electronic components as part of a processor unit which is configured to induce and detect the oscillation of the physical element. When the meter is connected to the sensor device, electrical conductivity is established between the processor unit and the conductive paths through the one or more physical elements in the sensor device. In some embodiments of the invention, oscillation at a particular frequency is induced in the physical element by the processor unit applying a time-varying actuation signal such as a voltage/current corresponding to the oscillation frequency through one or more conductive paths in the physical element. Similarly, a time-varying detection signal, such as a voltage/current, is measured by the processor unit through one or more conductive paths in the physical element in the vicinity of the oscillation frequency. In some embodiments of the invention, when the oscillation corresponds to a natural or fundamental resonance frequency of the physical element, the resonance characteristics are determined by actuating and detecting the oscillation in the physical element in a range of frequencies in the vicinity of the resonance frequency, for example, within a factor of 1.5, 2, 3, 4 or 5 of the resonance frequency. The resonance characteristics measured can include but are not limited to resonance amplitude, resonance frequency, Q-factor, etc. In some embodiments of the invention, where the oscillation in the physical element is induced and/or detected using electromagnetism, the actuating signal provided by the processor unit corresponds to a current injected/applied in the range of 100 nA to 10 A, for example, 100 µA to 1 A, through the conductive paths in the physical element in the presence of a magnetic field in the range of 0.001 T to 10 T, for example, 0.01 T to 2 T. In some embodiments, the detection signal measured by the processor unit corresponds to a voltage in the range of 0.01 µV to 10 V, for example, 1 µV to 1 V, in the presence of a magnetic field in the range of 0.001 to 10 T or 0.01 T to 2 T. In some embodiments, the amplitude of oscillation induced in the physical element is in the range of 1 nanometer to 100 microns, for example, 10 nanometers to 10 microns. The meter is provided with one or more enclosures to accommodate one or more permanent or variable magnets (such as an electromagnet) in the vicinity of a connector that provides conductivity to the one or more physical elements in the sensor device. In some embodiments of the invention, the meter is provided with top and bottom halves forming part of a clam-shell based assembly, that allows for the touchscreen display for the input and output interface, connector to the sensor device and the magnet to be enclosed in the top half, and the processor unit, battery, data port and power cord receptacle in the bottom half. The top and bottom halves can comprise one or more alignment fixtures that allow for precise assembly and securing or fastening of the two halves using means such as snap-fit assembly, screw-based compression assembly, etc.

In some embodiments of the invention, the meter may include a facility to sample environmental conditions such as temperature and apply a correction factor to the measurement response. Additionally the meter can have a memory facility that would allow previous readings to be stored and recalled, for example to provide a comparison of measurements across two or more dates or times. This feature may be of particular utility to an individual who undergoes regular testing as part of the monitoring of anti-coagulant levels such as Warfarin, Heparin, etc. in the blood. In some embodiments of the invention, in order to calibrate the machine or the individual sensor device, the meter may perform an initial self-test on the disposable strip prior to blood introduction.

Figure 1B:
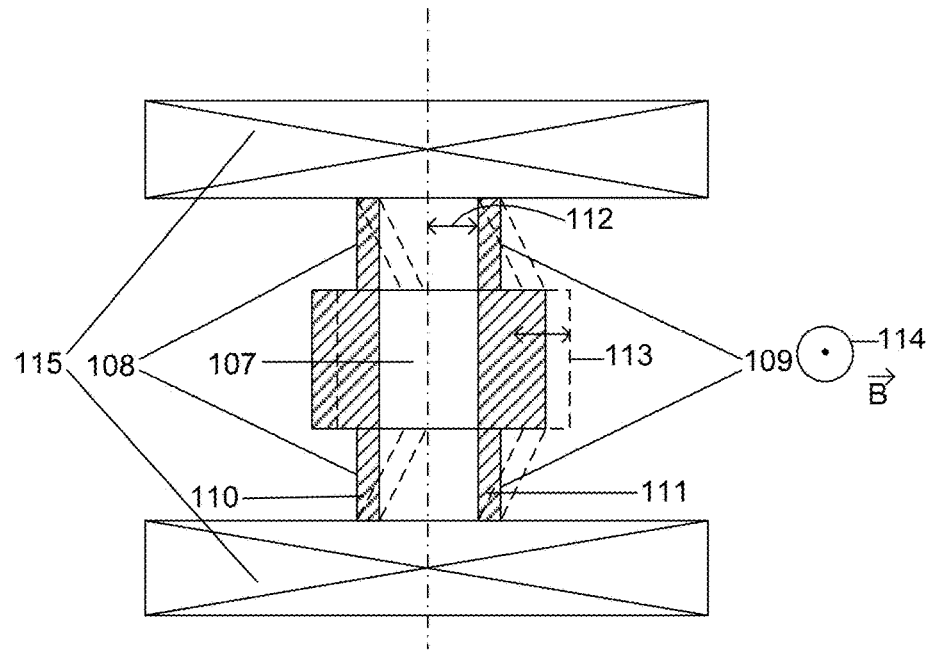
Figure 2:
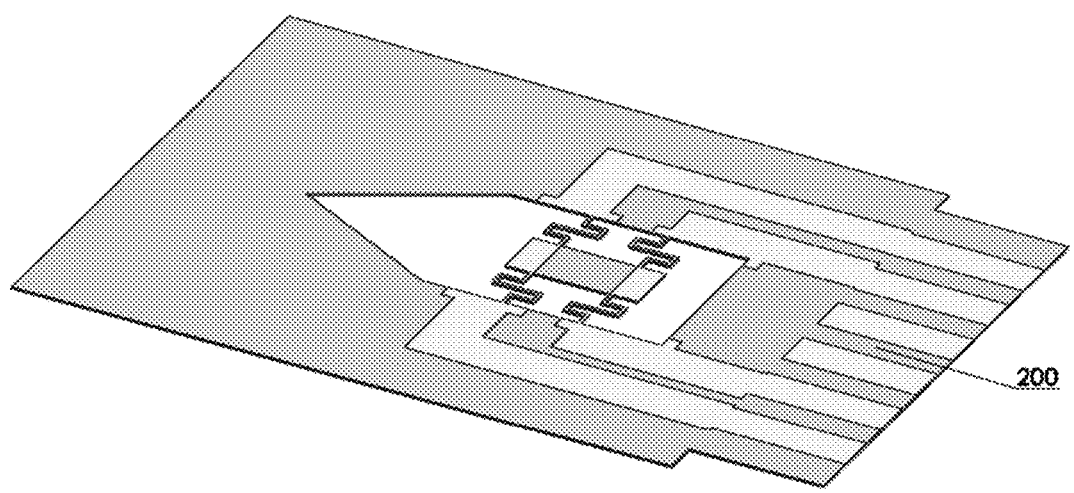
FIG. 2(a) depicts schematically an embodiment of a physical element sensing unit.
FIG. 2(b) shows an exploded view of a physical element sensing unit that illustrates the component layers which contribute thereto.
Figure 2:
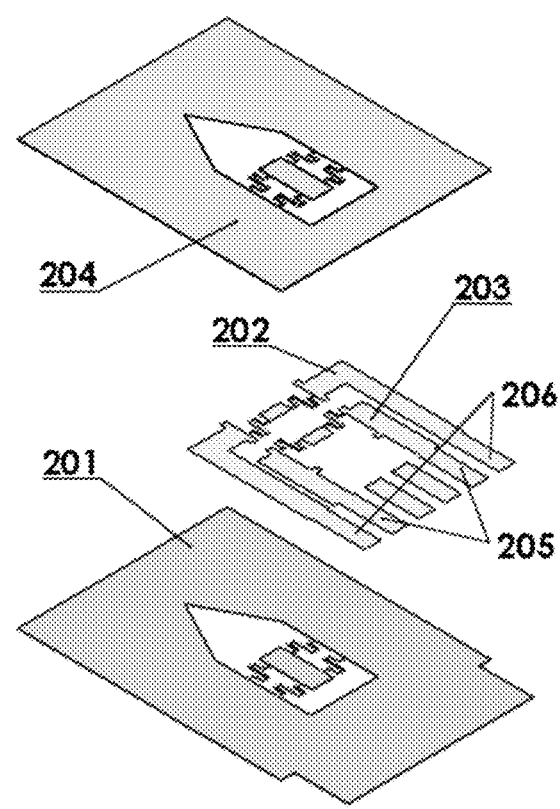

FIGS. 1(a) and 1(b) show schematics of two embodiments of substrate layers of the sensor devices of the invention which contain the physical element comprising the suspended element and compliant structures, the oscillation of which is used to determine the viscosity, viscoelasticity and/or density of a fluid, typically a liquid.

According to the first embodiment, as shown in FIG. 1(a), a substrate layer comprises a "physical element" (e.g., as a result of having been machined to form the physical element), which comprises a suspended element 101 and compliant structures 102, the compliant structures being attached to the suspended element at one end and the main body of the substrate layer 104 at the other. The main body of the substrate layer 104 is maintained to be stationary, indicated by the "X" mark across the structure, such that the physical element is configured to perform unimpeded motion or oscillations upon actuation. Also, the main body of the substrate layer 104 can be relatively larger than the suspended element 101. An electrically conductor 103 is formed and patterned on the substrate layer such that there is a conductive path through the physical element. A magnetic field 106 is applied in a direction perpendicular to the plane of the substrate layer. A time-varying current applied through the conductor 103 in the presence of a constant magnetic field 106 causes the physical element to oscillate in-plane; oscillation may be at the fundamental frequency or at a harmonic frequency of the physical element. Alternatively, a magnetic field 106 applied in the same plane as that of the physical element causes the physical element to oscillate out-of-plane; again, oscillation may be at its fundamental frequency, or at a harmonic frequency. The in-plane oscillations induced are indicated by the dotted line 105. The oscillation of an electrical conductor 103 in the presence of the magnetic field 106 electromagnetically induces a "detection voltage", which can be used to ascertain the characteristics of physical oscillatory movement in the structure. The shape and geometry of the suspended element 101 and compliant structures 102, and the exact location of the compliant structure relative to the suspended element and the stationary substrate layer 104 may be selected to obtain the optimum sensitivity for the measurement of fluid properties, ascertained by methods such as finite element analysis, empirical analysis, theoretical analysis, trial and error, etc. In addition, the geometry can be consistent with a relatively low or high oscillation harmonic frequency, resulting in a relatively large or small shear penetration depths ($\delta_s = \sqrt{\eta/\rho \pi f}$) into the fluid under concern respectively. Also, the amplitude of oscillation induced in the physical element can be controlled by the current applied through the conductor 103 subsequently controlling the shear rate ($\dot{\gamma}$) applied to the fluid.

In the embodiment of the substrate layer shown in FIG. 1(b), an alternative arrangement for the physical element is provided. The physical element is comprised of the suspended element 107 and two compliant structures 108 and 109 on each side of the symmetry line of the structure, the compliant structures being attached to the suspended element at one end and the main body of the substrate layer 115 at the other. The main body of the substrate layer 115 is maintained to be stationary, indicated by the "X" mark across the structure, such that the physical element is allowed to perform unimpeded motion or oscillations. Also, the main body of the substrate layer 115 can be relatively larger than the suspended element 107. Two electrical conductors 110 and 111 are formed and patterned on the substrate layer such that there are two independent and isolated conductive paths through the physical element. A magnetic field 114 is applied in a direction perpendicular to the plane of the substrate layer. A time-varying current applied through one or both conductors 110 and 111 in the presence of a constant magnetic field 114 cause the physical element to oscillate in-plane; oscillation may be at the fundamental frequency or at a harmonic frequency of the physical element. Alternatively, a magnetic field 114 applied in the same plane as that of the physical element causes the physical element to oscillate out-of-plane; oscillation may be at the fundamental frequency or at a harmonic frequency of the physical element. The in-plane oscillations induced are indicated by the dotted line 113. The oscillation of the electrical conductors 110 and 111 in the presence of the magnetic field 114 electromagnetically induces a "detection voltage", which can be used to ascertain the characteristics of physical oscillatory movement in the structure. The time-varying current and the detection voltage can be applied through either one of the electrical conductors 110 and 111 thus isolating the actuation and detection signals reducing crosstalk or interference. The shape and geometry of the suspended element 107 and the number of compliant structures 108 and 109, and the exact location of the compliant structures relative to the suspended element and the stationary substrate layer 115 may be selected to obtain the optimum sensitivity for the measurement of fluid properties, ascertained by methods such as finite element analysis, empirical analysis, theoretical analysis, trial and error, etc. In addition, the geometry can be consistent with a relatively low or high oscillation harmonic frequency, resulting in a relatively large or small shear penetration depths ($\delta_s = \sqrt{\eta/\rho\pi f}$) into the fluid under concern respectively. Also, the amplitude of oscillation induced in the physical element can be controlled by the current applied through the either one of the conductors 110 and 111 subsequently controlling the shear rate ($\dot{\gamma}$) applied to the fluid.

FIG. 2(a) shows embodiments of a substrate layer comprising a physical element which is suitable for measuring properties of a fluid, in particular a biological fluid, before and during a chemical reaction. As shown in FIG. 2(a), there is provided a substrate layer assembly 200 for integration into a disposable test strip embodiment of the sensor device of the invention.

FIG. 2(b) shows an exploded schematic of an assembly for integration into a disposable test strip. An substrate layer 201 is patterned to form a rectangular suspended element with 4 meandering compliant structures, the compliant structures being attached to the suspended element at one end and the main body of the substrate layer at the other. The physical element structure may be formed by any appropriate method, such as the conventional methods of laser, CNC milling or chemical etching or by stamping of the substrate layer. Independent and isolated patterned conductive tracks 202 and 203 are disposed on the substrate layer 201. These conductive tracks may be disposed by any appropriate method such the conventional methods of as screen printing or inkjet printing and can be composed of any suitably conductive and chemically inert material. A patterned insulating dielectric layer 204 is disposed onto the conductive tracks 202 and 203 such that the conductive tracks are completely insulated everywhere except on a region 205 and 206 dedicated to providing electrical connections to the physical element.

Figure 3:
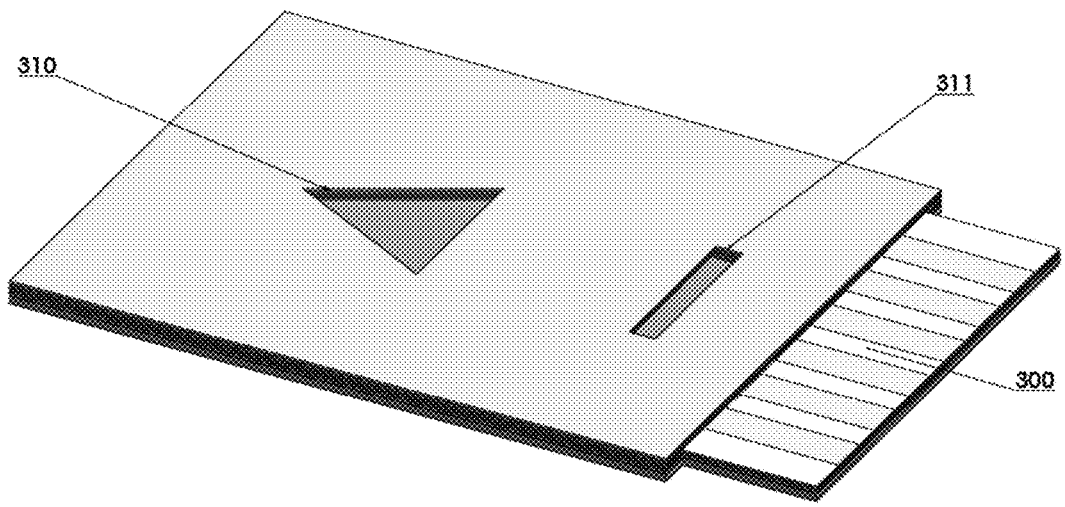
FIG. 3(a) shows a schematic view of a test strip for use in determining the viscosity, viscoelasticity and/or density of a fluid sample, in particular a body fluid such as blood.
FIG. 3(b) shows an exploded view of a test strip which illustrates the components therein.
Figure 3:
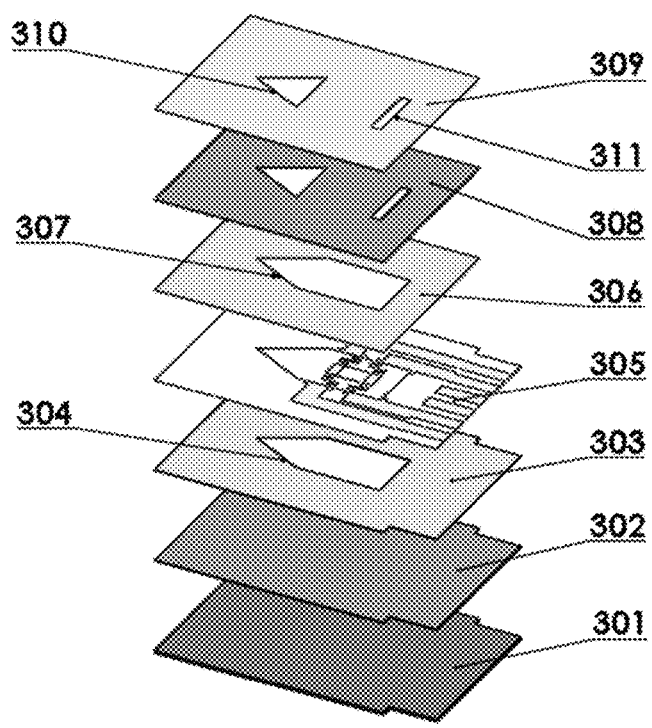

FIG. 3 illustrates a further embodiment. FIG. 3(a) shows a further embodiment of a sensor device in the form of a disposable test strip 300. FIG. 3(b) shows an exploded schematic of the disposable test strip 300 of FIG. 3(a). The disposable test strip 300 comprises a base substrate 301, onto which is disposed a hydrophilic wicking layer 302, which may optionally comprise a reagent to facilitate a chemical reaction. The reagent may be present as a sublayer. Alternatively, a reagent could be provided upon any internal surface of the chamber. A first chamber forming layer 303 is disposed onto the hydrophilic wicking layer 302. This chamber forming layer may be formed, e.g., using a patterned pre-cast film, or by screening printing or inkjet printing a suitable non-reactive polymeric material. The chamber forming layer is patterned to have a cut-out 304 to form the chamber wall, in the vicinity of the physical element allowing for it to be suspended for unimpeded motion or oscillation. The assembled "bottom stack" of layers comprise of the base substrate 301, hydrophilic layer 302 and first chamber forming layer 303. The reagent layer to facilitate the reaction in the chamber could alternatively be loaded onto the exposed surface of the hydrophilic wicking layer 302, after the "bottom stack" of the layers is assembled. A second chamber forming layer 306 is laminated to a second hydrophilic layer 308 also provided with a reagent layer, if needed. The chamber forming layer is patterned to have a similar cut-out 307, optionally but not necessarily the same, as in the first chamber forming layer 303 in the vicinity of the physical element allowing for it to be suspended for unimpeded motion or oscillation. A polymeric film 309 is then laminated onto the top of the second hydrophilic layer. The purpose of film 309 is to provide an upper seal layer on the reaction vessel and to protect the underlying structures of the remainder of the test strip from mechanical damage. The layers 301, 303 and 306 further improves the stiffness of the disposable test strip. The hydrophilic layer 308 and the polymeric film 309 are patterned to have a triangular 310 and a rectangular 311 opening, to serve as ports for introducing fluid into the strip and a vent to permit air to escape from the chamber as it is loaded with a fluid sample, respectively. The opening size, shape and geometry may be designed and selected to optimize the fluid introduction and air venting in the chamber.

A physical element sensor device assembly 305, such as that detailed in the embodiment depicted in FIGS. 2(a) and 2(b) may be laminated over the "bottom stack" comprising the base substrate 301, hydrophilic layer 302 and first chamber forming layer 303. The assembled "top stack" of layers, comprising the second chamber forming layer 306, hydrophilic layer 308 and the polymeric film 309, is disposed over and laminated on to the physical element sensor device assembly attached to the "bottom stack" of layers, such that the physical element is suspended within a "chamber" as defined by the hydrophilic layers 302 and 308, and the side-walls of the cut-outs 304 and 307 in the two chamber forming layers 303 and 306. The distance (D) between the bottom 302 or top 308 hydrophilic layers and the physical element sensor device assembly 305 as defined by the height of the two chamber forming layers 303 and 306, and the geometry of the cut-outs 304 and 307 in the chamber forming layers can be designed and selected to optimize the volume of the chamber, and optimize the fluid introduction and air venting in the chamber. The distance D or the height of the two chamber forming layers 303 and 306 can be further configured to have the oscillating physical element induce a standing shear-wave field in the fluid medium in the chamber, between the bottom 302 or top 308 hydrophilic layers and the physical element sensor device assembly 305. In order to have a consistent and reliable standing shear-wave field induced, depending on the fluid properties the distance D can be configured to be smaller than or equal to the shear penetration depth ($\delta_s = \sqrt{\eta/\rho\pi f}$). The lower the ratio of the distance D to the shear wavelength ($\lambda_s$) of the field induced in the medium surrounding the physical element, the higher is the consistency and uniformity of the acoustic field set up in the fluid medium, where $\lambda_s = 2\pi\delta_s/\sqrt{2} \cos(\delta_l/2)$ where $\delta_s$ is the shear penetration depth ($\delta_s = \sqrt{\eta/\rho\pi f}$) and $\delta_l$ is the loss-tangent angle of the medium. The distance D can be configured to be adjustable or permanently fixed depending on the properties of the fluid under concern introduced into the chamber, as noted above. The chamber forming layers 303 and 306 can be formed of single or multiple laminated polymeric substrates to tailor the distance D and, incorporated with pressure sensitive adhesives on both sides to facilitate the lamination to the physical element sensor device assembly 305 and the hydrophilic layers 302 and 308. The acoustic field setup in the fluid trapped between the physical element and the chamber walls can be used to not only determine the viscosity of the fluid but also its viscoelastic properties. Also, the presence of the fixed chamber walls close to the oscillating physical element offers additional benefits for high accuracy monitoring of the physical properties of the fluid as a function of time.

The structure and arrangement of the elements of the first and/or second chamber forming layer 303 and 306 may comprise two or more subsidiary, discrete pads arranged in relation to the main body of the chamber forming layers 303 and 306 in order to define an opening which allows a sample of fluid to be loaded into the chamber, which is defined by an internal volume provided within the sensor device. The fluid may be a biological fluid, for example blood. The arrangement of the two or more subsidiary pads which contribute to the first and/or second chamber forming layer 303 and 306, may be arranged in relation to the main body of the first and/or second chamber forming layer 303 and 306 in order to further provide at least one further channel or opening, typically provided at a different side of the chamber to the main opening, these secondary openings allowing for the side filling of liquids, or which, due to the opening being communicable with the central chamber, also permit air to escape from the chamber as it is loaded with a fluid sample.

Figure 4:
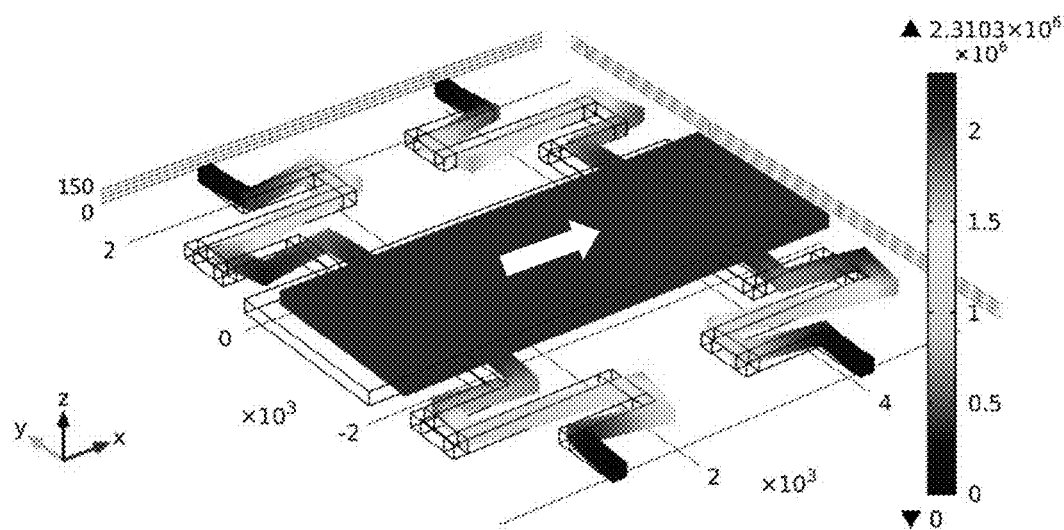
FIG. 4(a) shows a Finite Element Analysis (FEA) simulation of an embodiment (FIG. 2) of the physical element and its in-plane oscillations along the length (x-axis) direction.
FIG. 4(b) shows a Finite Element Analysis (FEA) simulation of an embodiment (FIG. 2) of the physical element and its in-plane oscillations along the width (y-axis) direction.
FIG. 4(c) shows a Finite Element Analysis (FEA) simulation of an embodiment (FIG. 2) of the physical element and its out-of-plane oscillations (z-axis).
Figure 4:
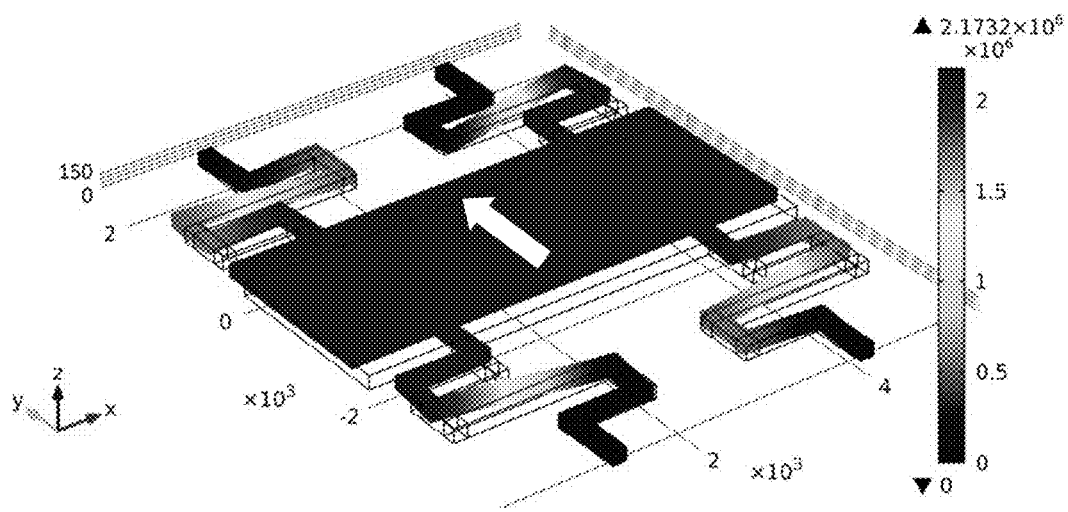
Figure 4:
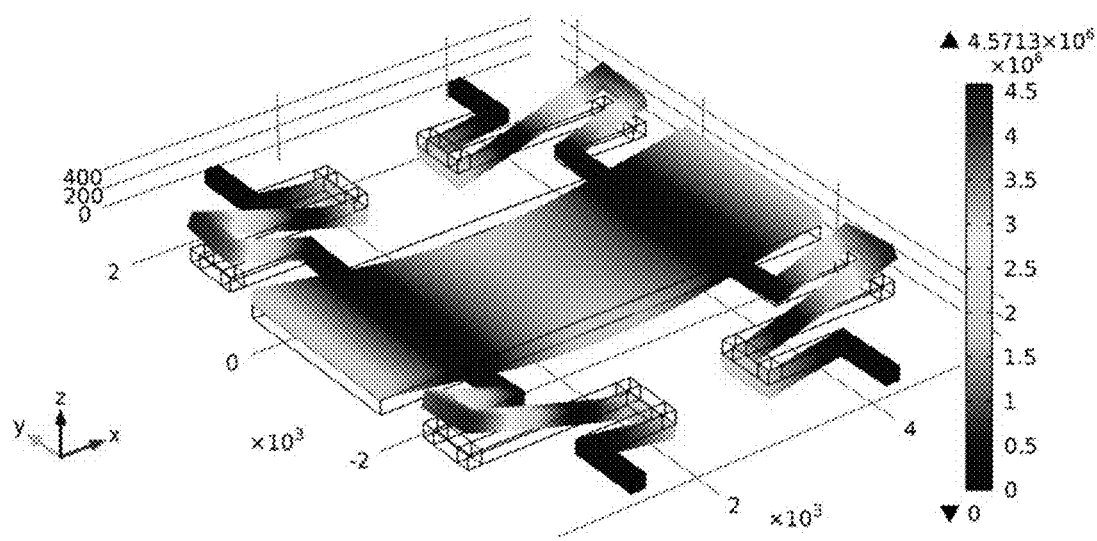
Figure 5:
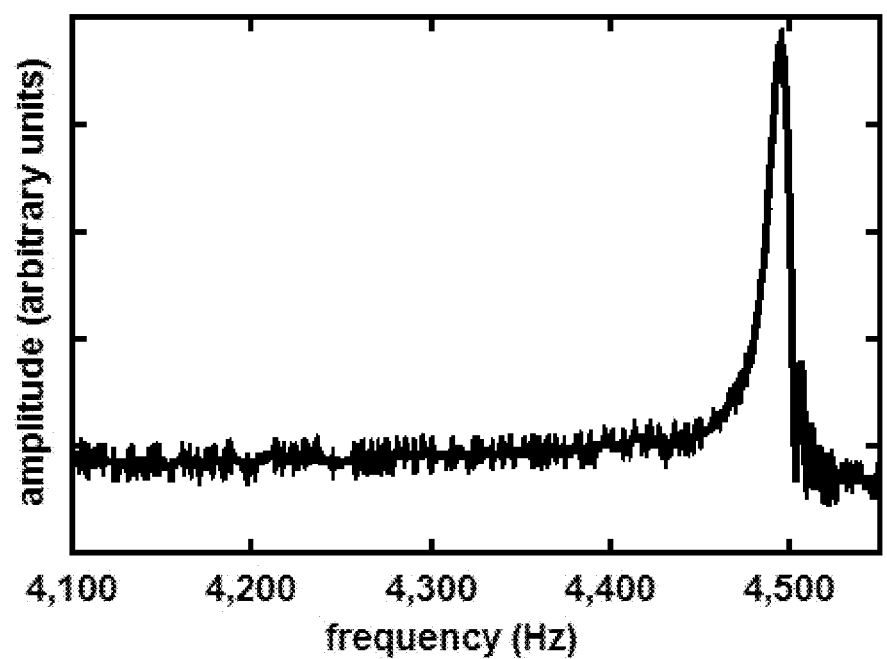
Figure 5:
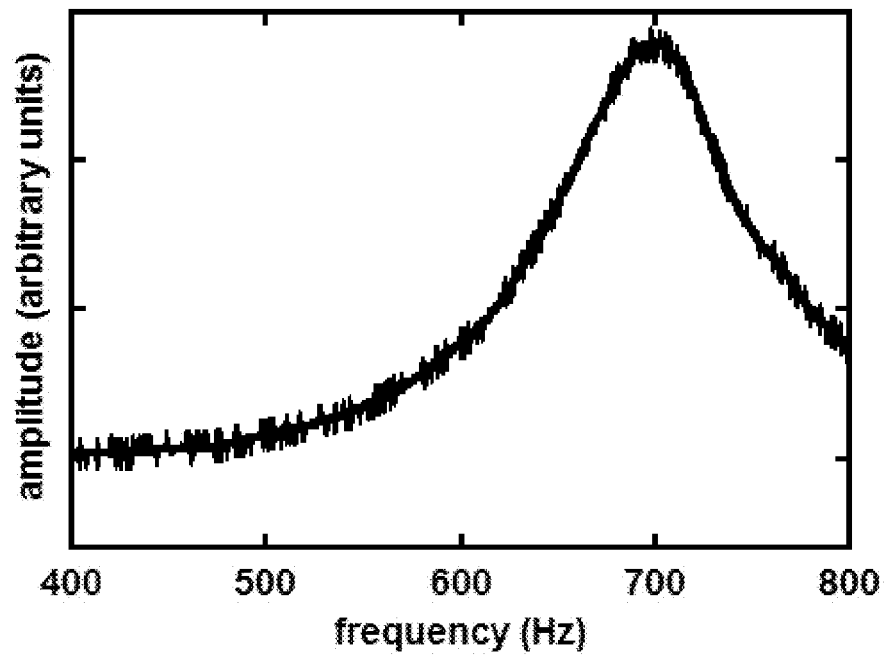
Figure 6:
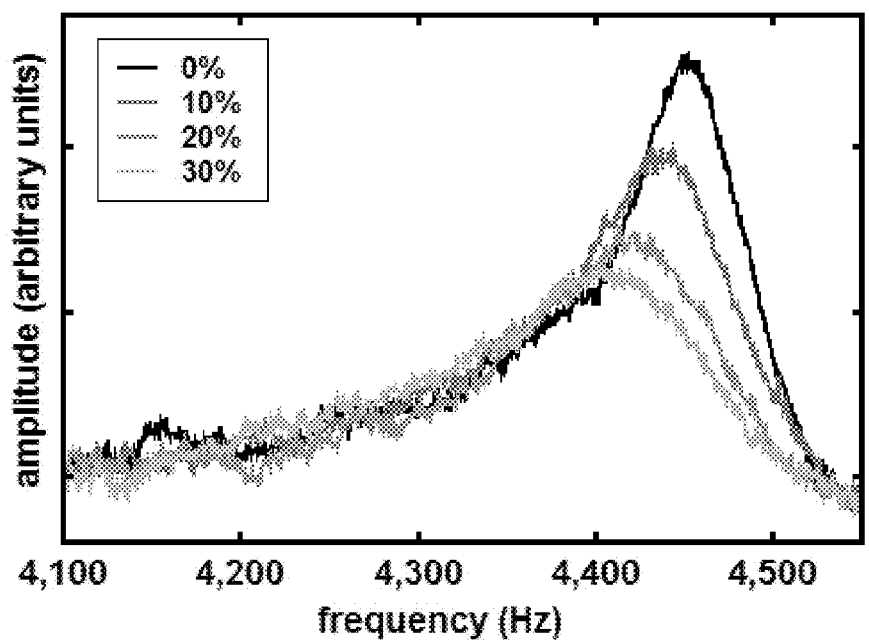
FIG. 6(a) shows a graph detailing the results of a frequency scan of in-plane oscillations of the physical element immersed in a range of aqueous (de-ionized water) solutions which contain ethylene glycol in different concentrations in order to determine how amplitude and frequency are affected by the viscosity and density of the liquid surrounding the oscillating physical element. The percentage values indicate the concentration (v/v) of ethylene glycol in deionized water.
FIG. 6(b) shows a graph detailing the results of a frequency scan of out-of-plane oscillations of the physical element immersed in a range of aqueous (de-ionized water) solutions which contain ethylene glycol in different concentrations in order to determine how amplitude and frequency are affected by the viscosity and density of the liquid surrounding the oscillating physical element. The percentage values indicate the concentration (v/v) of ethylene glycol in deionized water.
Figure 6:
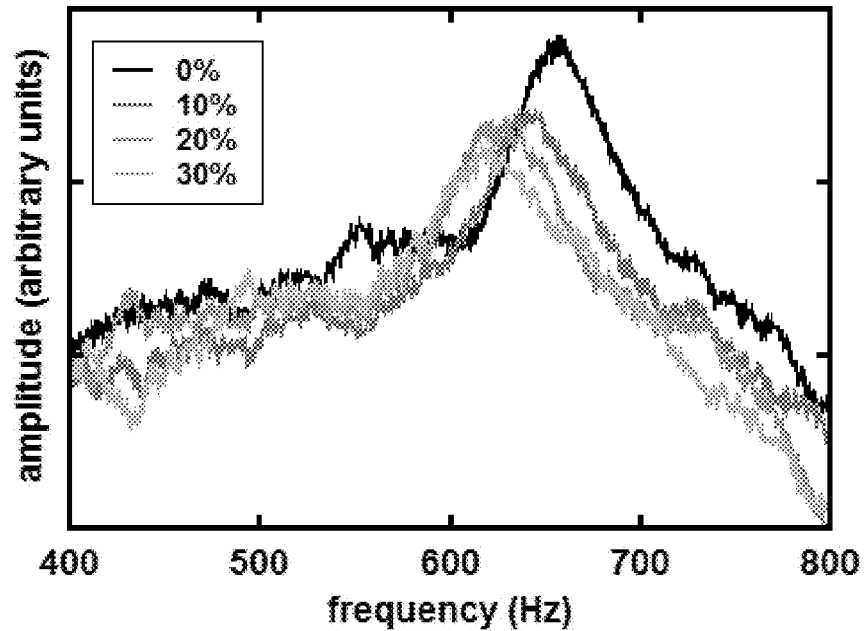

FIG. 4 shows in-plane (FIGS. 4(a) and 4(b)) and out-of-plane (FIG. 4(c)) oscillations computed using Finite Element Analysis (FEA) simulations induced in a physical element sensor device assembly, such as that detailed in the embodiment depicted in FIGS. 2(a) and 2(b), assembled in the form of a disposable test strip such as that detailed in the embodiment depicted in FIGS. 3(a) and 3(b). FIGS. 4(a) and 4(b) show the fundamental resonance of in-plane oscillations in the physical element in the direction of x-axis and y-axis respectively, which can be induced by fixing the direction of the magnetic field and varying the direction of the applied current or electric field applied to the physical element or, by varying the direction of the magnetic field and fixing the direction of the applied current or electric field applied to the physical element. FIG. 4(c) shows the fundamental resonance of out-of-plane oscillation in the physical element in the direction of z-axis, which can be induced by fixing the direction of the magnetic field and varying the direction of the applied current or electric field applied to the physical element or, by varying the direction of the magnetic field and fixing the direction of the applied current or electric field applied to the physical element. In an embodiment, the in-plane (FIGS. 4(a) and 4(b)) and out-of-plane (FIG. 4(c)) oscillations could be induced in a single or a combination of multiple physical elements, in a single or multiple individual chambers.

FIG. 5 through FIG. 8 are discussed in the Examples section below.

Figure 9:
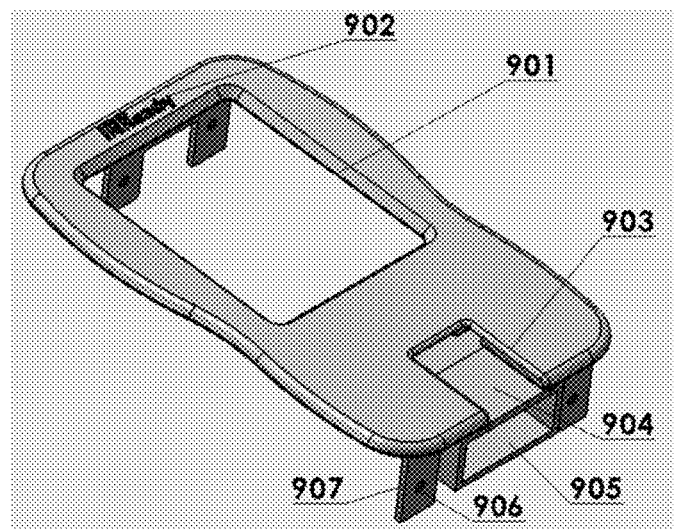
FIG. 9(a) shows a schematic of the top of an $\overline{\text{INR}}$eady meter chassis that is used to interface with a test strip to perform automated measurement of the fluid characteristics of a fluid introduced into the strip's chamber.
FIG. 9(b) shows a schematic of the bottom of an $\overline{\text{INR}}$eady meter chassis that is used to interface with a test strip to perform automated measurement of the fluid characteristics of a fluid introduced into the strip's chamber.
Figure 9:
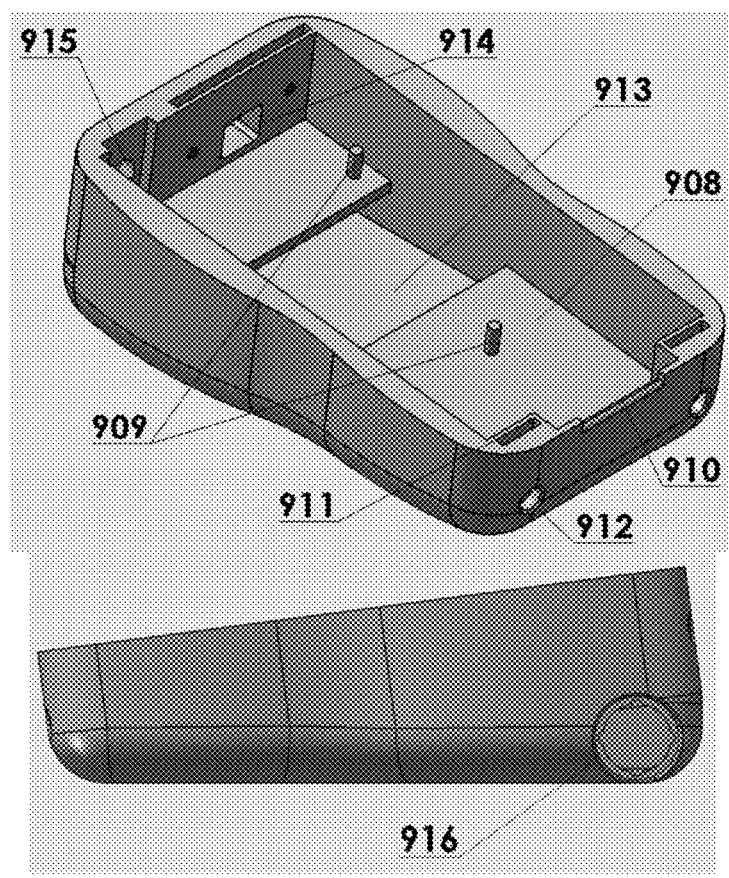

FIG. 9 illustrates an embodiment of a meter for interfacing with a disposable strip device according to the invention, such as that detailed in the embodiment depicted in FIGS. 3(a) and 3(b). FIGS. 9(a) and 9(b) show an embodiment of the top and bottom halves of the meter, housing a touch-screen display incorporated with a graphical user interface, electronic circuit boards and battery, which when assembled in a "clam-shell" based arrangement forms a solitary unit for interfacing with a disposable strip 300 to perform automated measurement of fluid properties. The top and bottom halves of the meter can be fabricated using standard techniques including but not limited to Stereolithography (SLA), injection molding, 3D printing, CNC milling, etc.

In the meter's top half embodiment (FIG. 9(a)), a logo by name INReady 902 is formed on the meter using Stereolithography. An opening 901 for the display on the meter is provided on the top half of the meter, which is provided with a touch-screen allowing for user interaction with the meter. A strip-enclosure 903 is provided on the top half to allow for the insertion of the disposable strip, and an electrical connector installed in the enclosure allows for electrical connectivity between the meter and the strip. A magnet-enclosure 905 is provided to hold a magnet providing a magnetic field, with the field lines intersecting the strip resting on a substrate 904 when inserted in the enclosure 903.

In the meter's bottom half embodiment (FIG. 9(b)) is provided with two compartments 908 and 913, which provide an enclosure for the electronics & display, and battery & power switch respectively. The compartment 908 holds the electronic circuit board with a display stacked on top, with alignment posts 909 to fix the position of the display with respect to the top and bottom halves of the meter. The compartment 913 encloses a lithium-ion, rechargeable battery that is used to power the electronic circuit board and display modules. Electronic access ports 915 and 914 are provided on the bottom half chassis for charging the battery and electronic connection to a computer for data access and retrieval respectively. A recess 916 is provided on the side of the bottom half chassis for installing a power button to switch the meter ON and OFF.

After installing the necessary components inside the bottom and top halves of the meter, the meter is assembled by aligning and inserting the fastening posts such as 907 provided on the top half of the meter, in to the recesses such as 911 provided on the bottom half of the meter. Further tapped through holes are provided through the fastening posts 907 and recesses 911 to allow for fastening the top and bottom structures together to form a solitary unit. Further, the strip-enclosure 903, substrate 904 and magnet-enclosure 905 align with a fillet 910 that is provided for ease of insertion of strip into the meter. In use, the disposable test strip would be inserted into the meter, such as that detailed in the embodiment depicted in FIGS. 9(a) and 9(b), so that the contacts provided at the end of the test strip device (205 and 206 shown in FIG. 2) opposite to the chamber, would provide direct electrical connection to the conductive pathways 202 and 203 through the physical element.

Figure 10:
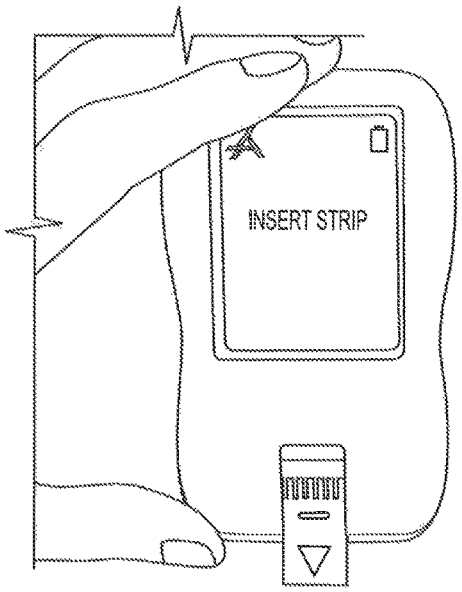
FIG. 10(a) shows the user-interaction work flow of interfacing the strip with the meter to perform blood based measurements (INR and TEG) viz. strip insertion into meter
FIG. 10(b) shows the user-interaction work flow of interfacing the strip with the meter to perform blood based measurements (INR and TEG) viz. meter prompting user to insert blood.
FIG. 10(c) shows the user-interaction work flow of interfacing the strip with the meter to perform blood based measurements (INR and TEG) viz. user collecting blood using a standard lancing device.
FIG. 10(d) shows the user-interaction work flow of interfacing the strip with the meter to perform blood based measurements (INR and TEG) viz. user introducing blood into the chamber through the top opening on the strip.
Figure 10:
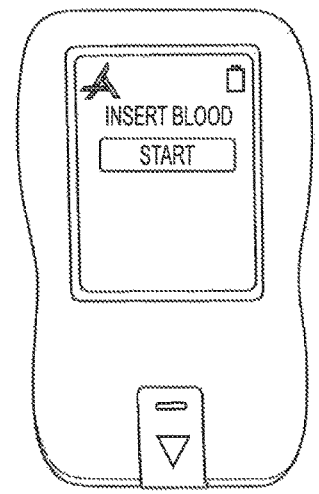
Figure 10:
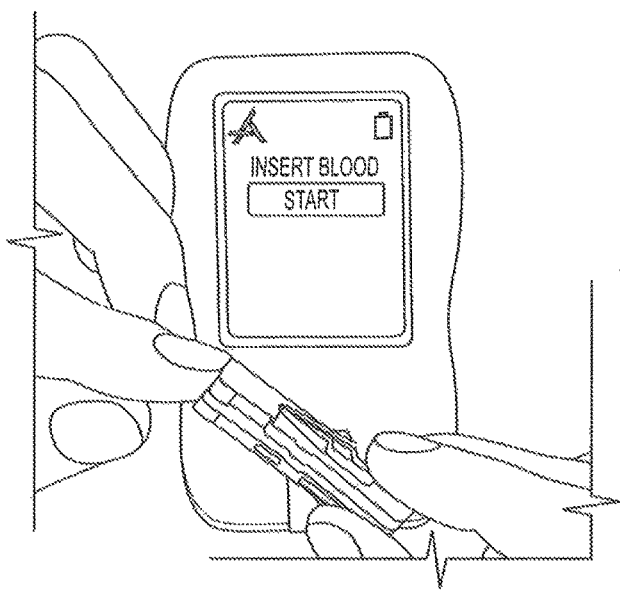
Figure 10:
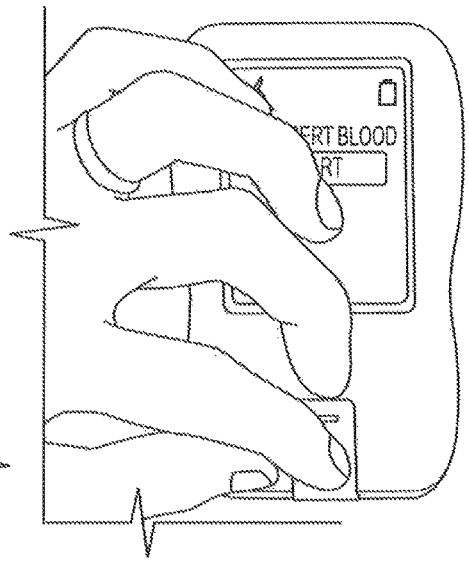

FIG. 10 shows the process flow of inserting a disposable test strip, such as that detailed in the embodiment depicted in FIGS. 3(a) and 3(b), into the meter to perform measurement on a fluid sample. In FIG. 10(a) the meter prompts the user to insert the strip into the enclosure. When the strip is inserted, the meter performs a calibration on the strip in preparation for measurement and prompts the user to insert blood as shown in FIG. 10(b). A small sample of biological fluid may be provided either directly from a wound site, or alternatively the biological fluid may be provided from a storage container or from an intermediate device such as a dropper which facilitates loading of the fluid into the chamber. Alternatively, the meter can be programmed to accept and analyze any fluid sample. In FIG. 10(c) the user uses a standard lancing device with a 21 gauge needle to supply a drop of blood to be introduced into the chamber in the strip.

A drop of fluid, in this case blood, when applied to the opening channel allows the fluid to enter into the main chamber 310 as seen in FIG. 10(d). Ingress of the fluid into the chamber through the opening is typically facilitated by a capillary action, this capillary effect resulting from the dimensions and arrangement of the channel. Other factors, such as the materials used in the construction of the sensor device may facilitate movement of the fluid into the chamber by capillary motion. As the fluid is drawn into the chamber, the air trapped in the chamber is allowed to vent out through the rectangular opening 311.

As blood is drawn into the chamber, the change in the fluid properties of the regions around the oscillating physical element results in changes in the oscillation characteristics of the structure, this including the electronics commencing analysis of the biological fluid sample. During a known time period, the analysis is completed and the change in viscosity, viscoelasticity and density of the fluid sample before, during and after the reaction is measured. After a suitable reaction time has passed, an algorithm would be used to convert the natural frequency signal and the quality factor measured into a usable test result.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

Example 1

Determining the Fluid Characteristics of Ethylene Glycol Aqueous Solutions Using a Physical Element Sensor Device Assembly Materials and Methods:

The physical element used in this example was fabricated by laser machining 3 mil stainless steel 316 sheets to define the suspended element and compliant structures essentially as shown in FIG. 2(a). The suspended element was fabricated in the shape of a rectangle with a length of 5 mm and width of 2 mm. Four compliant structures were fabricated in a meandering shape with a width of 0.125 mm and a total length of 5.526 mm. A fixture was made to clamp the other ends of the four compliant structures attached to the suspended element, and to provide electrical connectivity through the suspended element. The fixture was designed to have a chamber into which the physical element was suspended, which had fluidic ports to flow the liquid under concern through the chamber. A low-noise pre-amplifier (Stanford Research SR560) and a DSP lock-in amplifier (Stanford Research SR850) was used to apply the current through the suspended element and measure the "detection voltage" respectively. Two permanent magnets (sintered, N52 grade, 0.1-0.5 T) with radial and axial magnetic poling were used to provide magnetic field in parallel and perpendicular to the suspended element respectively. An enclosure was provided in the fixture which enabled fixing the relative position of the physical element and the magnet. Ethylene glycol solutions were prepared using de-ionized water in varying concentration ranging from 0 to 100% as shown in Table I. The solutions were prepared in 20 ml de-ionized water and corresponding volume of ethylene glycol solutions concentrations.

The solutions were introduced into the chamber so that the physical element was completely immersed and was then analyzed to ensure that there were no air bubbles present in the chamber. Current on the order of 10 mA at varying frequencies (detailed in the results section below) was introduced into the physical element via a first set of suspended elements along the short edge of the rectangular suspended element in the presence of a magnetic field in the range of 0.1 to 0.5 T depending on the distance from the surface of the magnet. When the magnetic field was applied perpendicular to the physical element, in-plane motion along the long edge of the rectangular suspended element (as seen in FIG. 4A) corresponding to the fundamental frequency of resonance was induced. When the magnetic field was applied parallel to the physical element, out-of-plane motion in a direction perpendicular to the rectangular suspended element (as seen in FIG. 4C) corresponding to the fundamental frequency of resonance was induced. The oscillation characteristics of the physical element viz. amplitude, frequency and quality factor were measured by measuring the "detection voltage" induced via electromagnetic induction at varying frequencies, along the second set of suspended elements along the short edge of the rectangular suspended element (on the opposite side as the first set). The quality factor was computed by the ratio of the measured resonance frequency to the width of the resonance peak as measured by the full width half max (detailed explanation provided in the definitions).

TABLE I

| Ethylene Glycol (v/v) [%] | Viscosity (cP) | Density (gm/cc) |
| --- | --- | --- |
| 0 | 1.0021 | 0.99822 |
| 3.12 | 1.2789 | 1.01093 |
| 4.87 | 1.4602 | 1.0177 |
| 6.77 | 1.6465 | 1.02452 |
| 10 | 1.9903 | 1.03508 |
| 16.22 | 2.7938 | 1.05178 |
| 20 | 3.3431 | 1.06 |
| 22.5 | 3.711 | 1.06479 |
| 30.03 | 4.9174 | 1.07657 |
| 40.38 | 6.8247 | 1.08806 |
| 53.73 | 9.6558 | 1.09784 |
| 72.32 | 13.7082 | 1.10616 |
| 100 | 20.8064 | 1.11323 |

Results:

Performance of Sensor in Air:

An example of a frequency scan in air for in-plane and out-of-plane oscillation of the physical element is shown in FIGS. 5(a) and 5(b) respectively. The frequency sweep for the in-plane and out-of-plane oscillations were performed in the ranges of 4100 to 4550 Hz, and 400 to 800 Hz to measure a resonance frequency of 4495 Hz and 700 Hz respectively.

Liquid Sensing Characteristics

The raw data from the frequency scans of the in-plane and out-of-plane modes of the physical element when immersed in ethylene glycol aqueous solutions of 0, 10, 20 and 30% is shown in FIGS. 6(a) and 6(b) respectively. Increasing concentrations of ethylene glycol dampen the sensor, such that the amplitude and frequency decreases. As the solutions become denser and more viscous it causes the physical element to oscillate more slowly through the liquid for both in-plane and out-of-plane modes, and correspondingly the frequency decreases.

Figure 7:
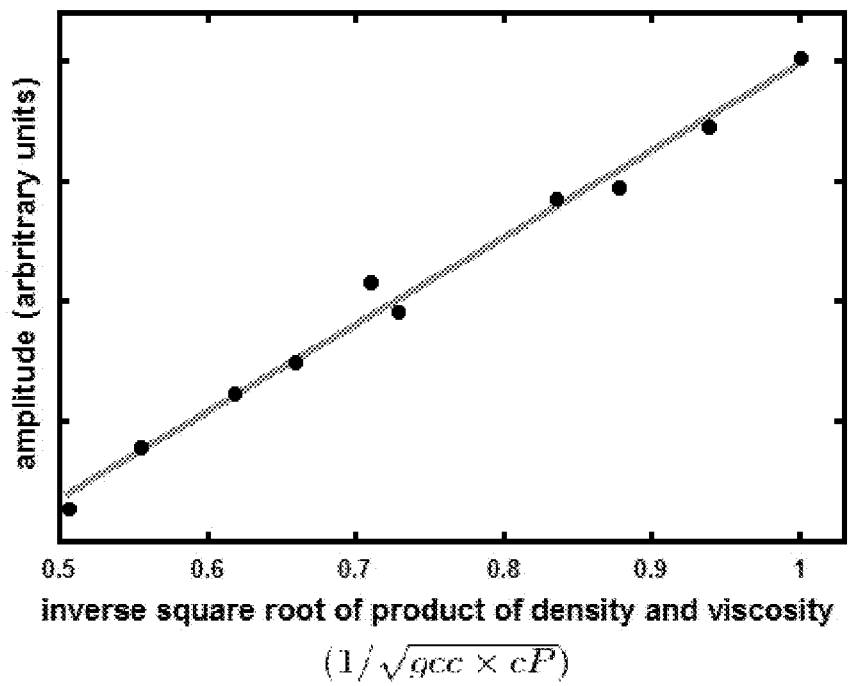
FIG. 7(a) shows a graph illustrating the relationship between fluid properties and response of the physical element undergoing in-plane oscillations i.e. amplitude for ethylene glycol solutions in de-ionized water.
FIG. 7(b) shows a graph illustrating the relationship between fluid properties and response of the physical element undergoing in-plane oscillations i.e. frequency for ethylene glycol solutions in de-ionized water.
FIG. 7(c) shows a graph illustrating the relationship between fluid properties and response of the physical element undergoing in-plane oscillations i.e. Q-factor (quality factor) for ethylene glycol solutions in de-ionized water.
Figure 7:
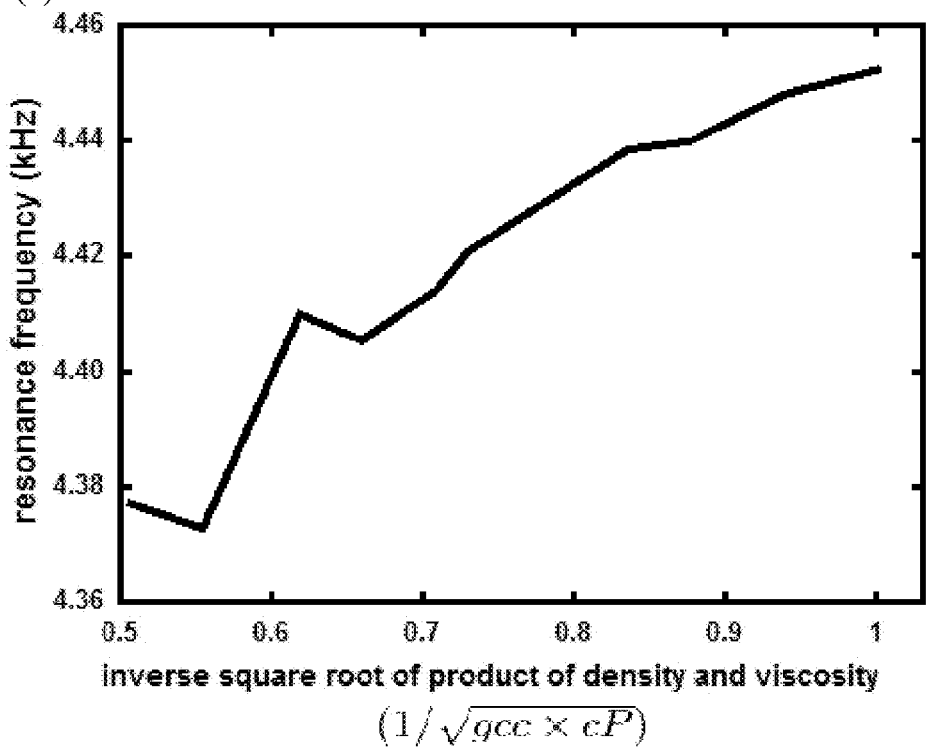
Figure 7:
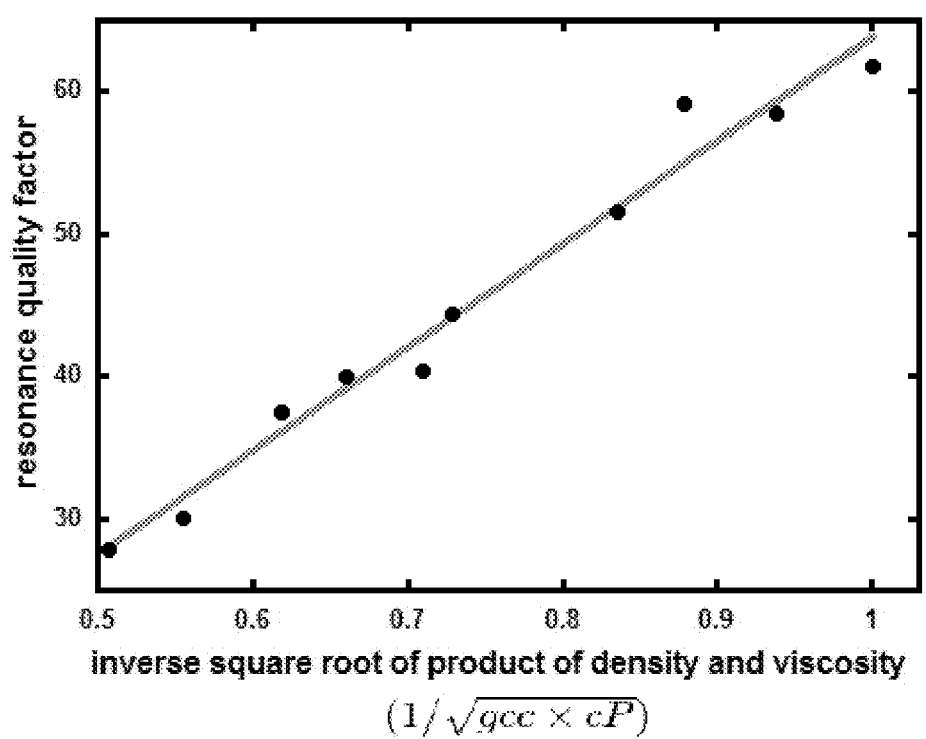

The analysis of the frequency scans from the in-plane mode of the physical element when immersed in varying concentrations of ethylene glycol is shown in FIG. 7. FIGS.

7(a) and 7(c) shows a linear relationship between the amplitude and quality factor, and the inverse square-root of the product of density and viscosity ($1/\sqrt{\eta\rho}$) of the ethylene glycol solutions. FIG. 7(b) shows a polynomial relationship between the in-plane resonance frequency and the inverse square-root of the product of density and viscosity ($1/\sqrt{\eta\rho}$) of the ethylene glycol solutions.

Figure 8:
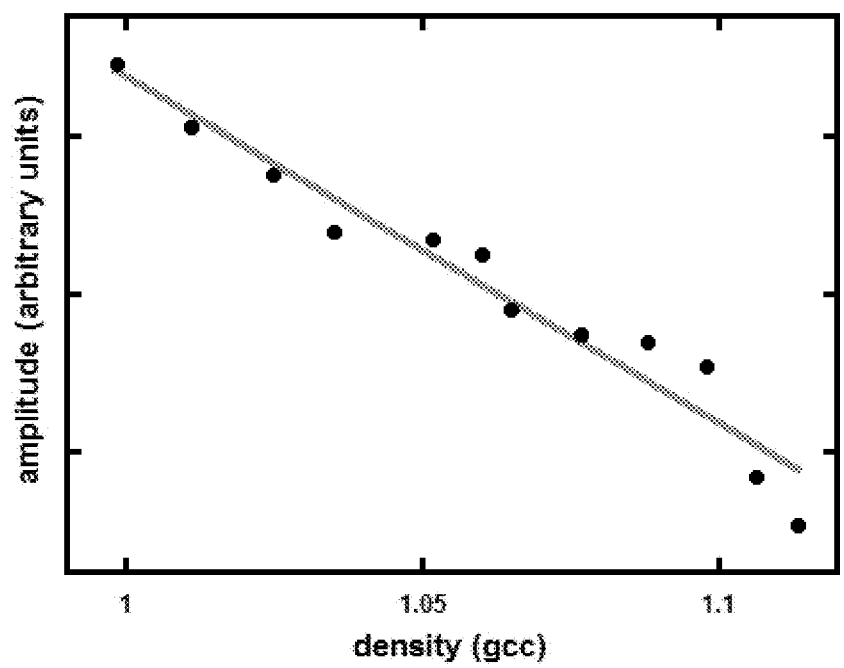
FIG. 8(a) shows a graph illustrating the relationship between fluid properties and response of the physical element undergoing out-of-plane oscillations i.e. amplitude for ethylene glycol solutions in de-ionized water.
FIG. 8(b) shows a graph illustrating the relationship between fluid properties and response of the physical element undergoing out-of-plane oscillations i.e. frequency for ethylene glycol solutions in de-ionized water.
Figure 8:
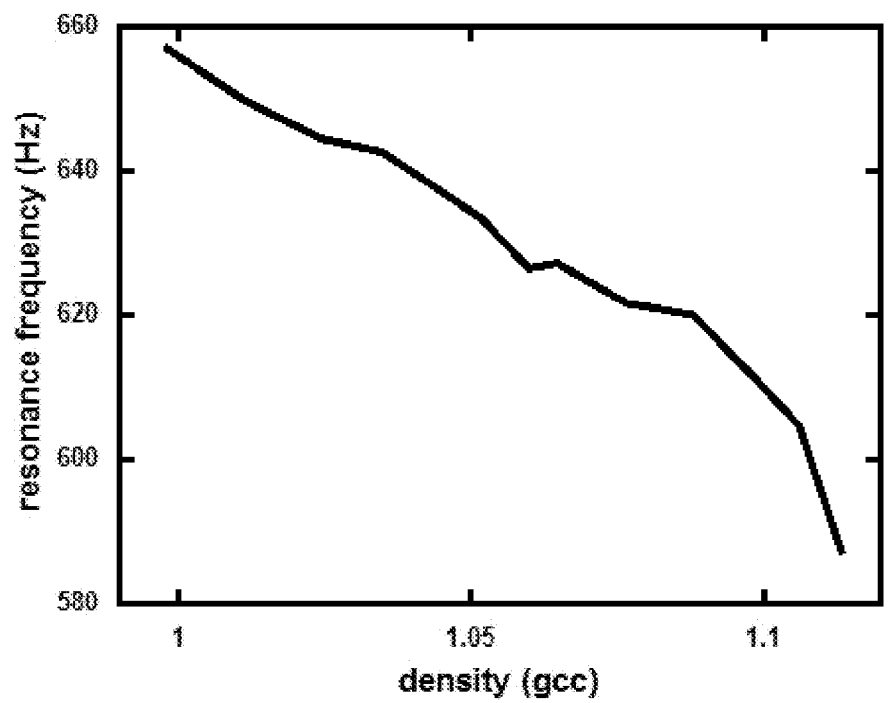

The analysis of the frequency scans from the out-of-plane mode of the physical element when immersed in varying concentrations of ethylene glycol is shown in FIG. 8. FIG. 8(a) shows a linear relationship between the amplitude and the density of the ethylene glycol solutions, and FIG. 8(b) shows a polynomial relationship between the out-of-plane resonance frequency and the density of the solutions.

By monitoring the in-plane and out-of-plane oscillations of the physical element, the viscosity and density of an arbitrary fluid can be deduced. The density of a fluid can be estimated from the out-of-plane mode characteristics and the viscosity-density product can be estimated from the in-plane mode, thus allowing for the independent and absolute measurement of density and viscosity of the fluid under concern. The sensor exhibited linearity in measuring the viscosity and density in the range of 1-20 cP and 0.998-1.113 gm/cc. This linearity enables the accurate determination of the absolute values of blood viscosity and density with typical ranges of 5-20 cP and 1.032-1.080 gm/cc respectively. In addition, since the density is linearly related to the hematocrit in a blood sample by the simple relationship $\rho=1.026+0.067$Hct gm/cc hematocrit can be accurately ascertained from the measured blood density, since the device operation was demonstrated to be linear in that range as shown in FIG. 8.

Example 2

Determining of the INR and TEG of Human Blood Using a Physical Element Sensor Device Assembly Materials and Methods:

FIG. 3(b) shows an exploded schematic of the disposable test strip 300 of FIG. 3(a). The strip was fabricated and assembled using standard diagnostic test strip manufacturing materials made of polyester-based substrates with acrylic adhesives to hold the structure in place.

Strip Bottom Stack Assembly:

The base substrate 301 was composed of 2 layers of a single-sided pressure sensitive adhesive (PSA) with a total thickness of 0.0124" (8259, Adhesives Research, Inc.) to provide structural support. A polyester substrate with a hydrophilic wicking layer on one side 302 with a thickness of 0.0045" (ARFlow 90469, Adhesives Research, Inc.) was laminated onto the base substrate, with the hydrophilic side facing away from the base substrate. A first chamber forming layer 303, composed of a double-sided PSA with a thickness of 0.0034" (9965, 3M, Inc.), was patterned to have a cut-out 304 to form the chamber wall in the vicinity of the physical element. The assembled "bottom stack", comprising of the base substrate 301, hydrophilic layer 302 and the first chamber forming layer 303, was patterned to form the foot-print of the strip (1.6×2.5 cm$^2$) surrounding the chamber as shown in FIG. 3. The reagent layer to facilitate the reaction in the chamber could alternatively be loaded onto the exposed surface of the hydrophilic wicking layer 302, after the "bottom stack" of the layers is assembled.

Strip Top Stack Assembly:

A second chamber forming layer 306 fabricated in the same manner as the first chamber forming layer was laminated to a second hydrophilic layer 308. The chamber forming layer was patterned to have a similar cut-out 304 as in the first chamber forming layer 303. A clear polyester film 309 (CG3300, 3M, Inc.), with a printed graphic consisting of the company logo and location of blood drop introduction, was then laminated onto the top of the second hydrophilic layer on the side not containing the hydrophilic layer. The purpose of film 309 was to provide an upper seal layer on the chamber and to protect the underlying structures of the remainder of the test strip from mechanical damage. The hydrophilic layer 308 and the polymeric film 309 were patterned to have a triangular 310 and a rectangular 311 opening, to serve as ports for introducing fluid into the strip and to vent to permit air to escape from the chamber as it was loaded with a fluid sample, respectively. The assembled "top stack", comprising of the second chamber forming layer 306, hydrophilic layer 308 and the polymeric film 309, was patterned to form the foot-print of the strip (1.6×2.5 cm$^2$) surrounding the chamber as shown in FIG. 3.

Physical Element Fabrication:

A physical element sensor device was made by screen printing silver-based conductive ink on a 0.003" clear polyester substrate to pattern the electrically conductive paths through the physical element and provide electrical pads to connect to the meter. The physical element comprised of the suspended element and compliant structures were patterned by laser machining the polyester substrate with the conductive ink. The suspended element was fabricated in the shape of a rectangle with a length of 5 mm and width of 2 mm. Four compliant structures were fabricated in a meandering shape with a width of 0.125 mm and a total length of 5.526 mm.

Prothrombin Time Reagent Incorporation:

The physical element sensor device, assembled "bottom stack" and "top stack" of the strip were incorporated with a reagent comprising of rabbit brain thromboplastin (Pacific Hemostasis Prothrombin Time reagent, Thromboplastin-DS, Product #29-227-3), calcium chloride (25 mM) and Tween (2% v/v aqueous solution). The reagent was incorporated by dropping the solution with a pipette on to the exposed hydrophilic layers in the top and bottom stacks of the strip (10 µl each) and, on the top and bottom of the physical element sensor device assembly 305 (10 µl each), followed by air drying for >7 hours at standard room temperature and relative humidity. The ratio of the volume of the reagent to blood that could be contained in the chamber was maintained at 2:1, with 30 µl of reagent and 15 µl of blood.

Strip Assembly:

The physical element sensor device was laminated over the bottom stack loaded with reagent. The assembled top stack was disposed over and laminated on top of the physical element sensor device assembly attached to the bottom stack of layers, such that the physical element was suspended within a chamber as defined by the hydrophilic layers 302 and 308, and the side-walls of the cut-outs 304 and 307 in the two chamber forming layers 303 and 306. The distance (D) between the bottom 302 or top 308 hydrophilic layers and the physical element sensor device assembly 305 as defined by the height of the two chamber forming layers 303 and 306 (0.01"), and the geometry of the cut-outs 304 and 307 in the chamber forming layers, were selected to have a total blood volume contained by the chamber to be 15 µl. The blood wicked into the chamber when it was introduced into the triangular opening 310, and displaced the air in the chamber through the rectangular opening 311.

The meter used to perform the measurement was fabricated using standard steriolithography SLA processes with a design as shown in FIG. 9. A custom printed circuit board with a microcontroller was provided in the meter to actuate the physical element sensor device embedded in the strip by injecting/applying time-varying currents through the conductive paths at oscillation frequencies in the vicinity of the resonance frequency of the physical element. The meter was provided with a standard resistive touch-screen display with a graphical user interface to interact with the instrument for example to start the measurement, and to display the results in real-time as shown in FIG. 10.

Figure 11:
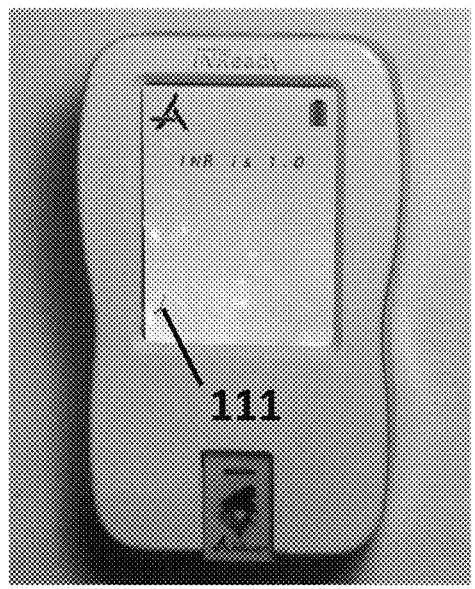
FIG. 11(a) shows the blood coagulation test INR performed on a sample of blood with a real-time plot of the instantaneous blood viscosity displayed on the screen.
FIG. 11(b) shows the blood coagulation tests INR and TEG performed on the same sample of blood with a plot of the blood viscoelasticity displayed on the screen.
Figure 11:
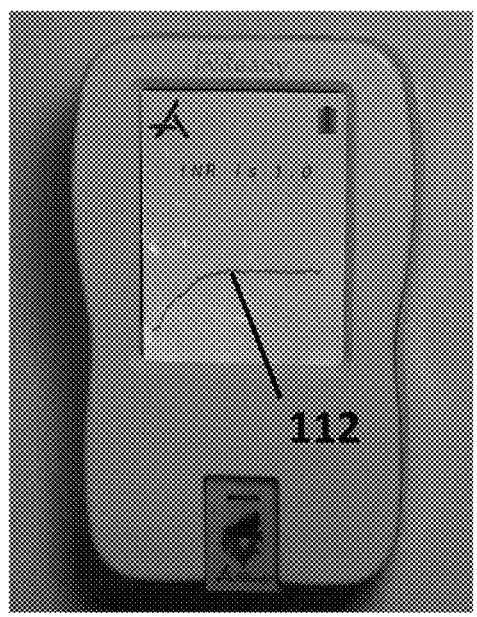

Results:

Blood coagulation tests were performed using the strip and meter following the workflow detailed in FIG. 10 as previously described. When blood was introduced into the chamber of the strip as per the workflow detailed in FIG. 10, coagulation was induced as the blood flowed into the chamber and mixed with the dried reagent incorporated in the chamber. Before and during blood coagulation, the absolute blood viscosity was measured instantaneously using the in-plane oscillation characteristics of the physical element and was plotted on the meter display as shown in FIG. 11. The Prothrombin Time (PT) of the blood was calculated based on the rate of increase in blood viscosity as a function of time 111, and the deduced International Normalized Ratio (INR) was displayed on the screen in less than 30 seconds as shown in FIG. 11(a). After the blood clot was formed, the measurement of in-plane vibration was continued and the viscoelastic properties of the blood clot formed between the physical element sensor device assembly and the hydrophilic layers in the chamber was determined. The blood viscoelasticity was plotted on the screen as shown in FIG. 11(b), which could be representative of a standard blood test known as the thromboelastograph (TEG) 112. The amplitudes of the blood viscosity 111 and viscoelasticity 112 as plotted on the screen were shown in arbitrary values to represent the fluid property variation trend/profile as the blood clots. This demonstrates the capability of the meter and strip to perform multiple blood coagulation tests on the same blood sample.

Listing of Features and Embodiments

The following list provides additional features that may be present in devices and/or methods according to the invention.

1. The substrate layer may be composed of a material which is selected from a group of materials including polymers such as polyester (PET), plastics, printed circuit board, etc., and/or may be fabricated using mass manufacturing methods including roll-to-roll continuous flow manufacturing.
2. The suspended element and compliant structures of the substrate layer may be patterned/formed by a technique selected from etching, laser treatment, printing and mechanical punching/cutting.
3. An electrically conductive path running across compliant structures and a suspended element may comprise pure metals (Silver, Gold, Palladium, Titanium, Tungsten, Platinum, Stainless Steel, etc.), metal alloys, conductive polymers, etc, and/or the electrical path may be incorporated on top, bottom, inside or as part of the active substrate.
4. An electrically conductive path running across compliant structures and a suspended element may be formed by a technique selected from metal evaporation, thin metal film extrusion, printing or laser treatment.
5. When actuating oscillation of and measuring signal from a suspended element, an electrical field can be applied and a detection signal can be measured across independent electrically conductive pathways.
6. When actuating oscillation of and measuring signal from a suspended element, vibration can be induced through a time-varying electrical field and constant magnetic field, or a constant electrical field and time-varying magnetic field. The time-varying field may correspond to at least one of the suspended element's fundamental or harmonic frequencies of vibration.
7. The detection signal resulting from oscillation of the suspended element monitored in a range of frequencies in the vicinity (e.g., within a factor of 1.5, 2, 3, 4 or 5) of the frequency of the time-varying excitation field or fields.
8. Oscillation of a suspended element or of two or more independent suspended elements may be induced at two or more frequencies, and the oscillations may comprise two in-plane oscillations at different frequencies and/or an in-plane oscillation and an out-of-plane oscillation.
9. The upper and lower layers of a device according to the invention can be positioned at a fixed or adjustable distance above and below the substrate layer, and/or the substrate layer can be clamped or affixed to the upper and lower substrates everywhere except the suspended element(s) and attached compliant structures.
10. Methods according to the invention can comprise inducing a standing shear-wave field in the medium between a suspended element and one or both of the upper and lower layers.
11. Devices according to the invention may comprise additional layers such as those shown in FIG. 3(b).
12. One or more layers of a device according to the invention may comprise at least one channel or opening suitable to permit the entry of a fluid sample into the reaction chamber, which optionally may be of suitable dimensions such that the fluid sample can enter into said reaction chamber by means of capillary action, and/or at least one channel or opening suitable to permit the displacement of air therethrough upon the filling of the reaction chamber with a fluid sample.
13. At least one surface of the chamber of a device may have a low contact angle with fluids (e.g., less than or equal to 45 degrees), which can facilitate substantially full occupancy of the chamber by an aqueous fluid sample.
14. Methods may comprise computing static or dynamic viscoelastic properties of a fluid from the measured viscosities and/or density of fluid at different applied shear rates ($\dot{\gamma}$); theoretical or empirical models may be used in such computations.
15. A change in one or a combination of oscillation characteristics of at least one suspended element may be used in methods to determine the fluid properties before, during and/or after a chemical reaction in the sample.
16. Methods in which a blood sample is analyzed may comprise bringing a blood sample into contact with at least one blood clotting agent before, during or after introduction of the sample into a chamber, wherein the oscillation characteristics of at least one suspended element are used to determine blood fluid properties and blood clotting reaction dynamics such as clotting time in PT, PTT, and/or ACT coagulation tests.
17. Methods in which a blood sample is analyzed may comprise determining the concentration of red blood cells or hematocrit in the blood sample. This determination may be performed or may use data acquired prior to bringing the fluid into contact with a clotting reagent. Blood clotting reaction dynamics and/or blood fluid properties may be calibrated or adjusted using the measured hematocrit.

18. When analyzing a blood sample comprising an anticoagulant, methods may comprise determining the concentration of anticoagulant in the blood sample. This may be performed or may use data acquired prior to bringing the blood sample into contact with the clotting reagent.

The following list provides additional non-limiting examples of systems and methods contemplated according to the invention.

1. A system for measuring a fluid, comprising:
    a fluidic resonator configured to apply a shear rate and stress to the fluid;
    a sensor configured to measure a vibration of the fluidic resonator during application of the applied shear rate and stress; and
    a processor configured to identify a parameter indicative of a viscosity and/or density of the fluid based on a damping of the vibration of the resonator caused by the fluid at a fixed applied shear rate/stress.
2. The system of embodiment 1, wherein the sensor is configured to measure at least one of (a) a quality factor of the vibration, (b) a resonance frequency of the vibration, (c) an amplitude of the vibration, and (d) a phase of the vibration.
3. The system of embodiment 1, wherein the sensor is configured to measure a combination of (a) a quality factor of the vibration, (b) a resonance frequency of the vibration, (c) an amplitude of the vibration, and (d) a phase of the vibration.
4. The system of embodiment 1, wherein the resonator is a purely in-plane resonator.
5. The system of embodiment 1, wherein the resonator is a purely out-of-plane resonator.
6. The system of embodiment 1, further comprising:
    a thermal sensor configured to sense a temperature of the fluid during the measurement of the vibration; and
    a thermal actuator configured to control a temperature of the fluid during the measurement of the vibration.
7. A method of measuring a fluid, comprising:
    applying a shear rate and stress to the fluid via a fluidic resonator;
    measuring a vibration of the fluidic resonator during the application of the applied shear rate and stress; and
    identifying a parameter indicative of a viscosity and/or density of the fluid based on a damping of the vibration of the resonator caused by the fluid, at a fixed applied shear rate/stress.
8. The method of embodiment 7, wherein:
    the measured vibration is an in-plane vibration of the fluidic resonator at a frequency f at a fixed applied shear rate/stress such that the penetration depth of the shear wave ($\delta_s = \mathrm{Sqrt}(\eta/\rho\pi f)$) is relatively small; and
    the identified parameter is indicative of the viscosity of the constant phase ($\eta_{cp}$) of a complex non-Newtonian fluid.
9. The method of embodiment 7, wherein:
    the measured vibration is an in-plane vibration of the fluidic resonator at a frequency f at a fixed applied shear rate/stress such that the penetration depth of the shear wave ($\delta_s = \mathrm{Sqrt}(\eta/\rho\pi f)$) is relatively large, and
    the identified parameter is indicative of the viscosity of the bulk ($\eta_{bulk}$) of a complex non-Newtonian fluid.
10. The method of embodiment 7, wherein the identified parameter is indicative of a concentration of an additive ($c_s$) in a non-Newtonian fluid,
11. The method of embodiment 10, wherein the non-Newtonian fluid includes particulates or solid-phase objects.
12. The method of embodiment 7, further comprising:
    identifying a standardized measure of bulk viscosity of a complex non-Newtonian fluid at a standardized additive concentration as a function of the fluid's properties.
13. The method of embodiment 12, wherein the standardized measure is identified as a function of one or more of viscosity of constant phase of fluid ($\eta_{cp}$), viscosity of bulk of fluid ($\eta_{bulk}$) and concentration of additive ($c_s$).
14. The method of embodiment 7, further comprising:
    computing static or dynamic, as a function of time, viscoelastic properties of a complex non-Newtonian fluid from the measured viscosities and/or densities of fluid at different applied shear rates ($\dot{\gamma}$) using different theoretical or empirical models.
15. The method of embodiment 14, wherein the viscoelastic properties include yield stress ($\tau_y$).
16. The method of embodiment 14, wherein the viscoelastic properties are determined according to Casson's model—

$$\eta_{bulk} = \frac{\left(\sqrt{\tau_y} + \sqrt{k\dot{\gamma}}\right)^2}{\dot{\gamma}}.$$

17. The method of embodiment 7, further comprising:
    computing static or dynamic viscoelastic properties of a complex non-Newtonian fluid, from the standardized bulk viscosities of fluid computed at different concentrations of additive ($c_s$) and applied shear rates ($\dot{\gamma}$) using different theoretical or empirical models, thereby allowing for identification of an empirical relationship between the fluid property and concentration of additive ($c_s$).
18. The method of embodiment 17, wherein the viscoelastic properties include yield stress ($\tau_y$).
19. The method of embodiment 17, wherein the viscoelastic properties are determined according to Casson's model—

$$\eta_{bulk} = \frac{\left(\sqrt{\tau_y} + \sqrt{k\dot{\gamma}}\right)^2}{\dot{\gamma}}.$$

LIST OF REFERENCES CITED

1. G. D. O. Lowe, "Blood rheology in arterial disease," *Clinical Science*, vol. 71, pp. 137-146, 1986.
2. G. D. O. Lowe, "Blood rheology and vascular disease," *Haemostatsis and Thrombosis* (ed. by A. L. Bloom et al), 3rd edn, pp. 1169-1188. Churchill Livingstone, Edinburgh, 1994.
3. L. Dintenfass, "Blood Microrheology: viscosity factors in blood flow ischaemia and thrombosis," Butterworth, London, 1971.

4. G. D. O. Lowe, W. C. S Smith, H. D. Tunstall-Pedoe, I. K. Crombie, S. E. Lennie, J. Anderson, J. C. Barbenel, "Cardiovascular risk and haemorheology: results from the Scottish Heart Health Study and the MONICA project, Glasgow," *Clinical Haemorheology*, vol. 8, pp. 518-524, 1988.
5. G. D. O. Lowe, A. J. Lee, A. Rumley, J. F. Price, F. G. R. Fowkes, "Blood viscosity and risk of cardiovascular events: the Edinburgh Artery Study," *British Journal of Haematology*, vol. 96, pp. 168-73, 1997.
6. G. Ciuffetti, G. Schillaci, R. Lombardini, M. Pirro, G. Vaudo, E. Mannarino, "Prognostic impact of low-shear whole blood viscosity in hypertensive men," *European Journal of Clinical Investigation*, vol. 35 no. 2, pp. 93-98, February 2005.
7. R. Rosencranz, S. A. Bogen, "Clinical laboratory measurement of serum, plasma, and blood viscosity," *American Journal of Clinical Pathology*, vol. 125, Suppl. 1, pp. S78-S86, 2006.
8. A. Matrai, R. B. Whittington, E. Ernst, "A simple method of estimating whole blood viscosity at standardized hematocrit," *Clinical Haemorheology*, vol. 7, pp. 261-265, 1987.
9. W. I. Rosenblum, "In vitro measurements of the effects of anticoagulants on the flow properties of blood: The relationship of these effects to red cell shrinkage," *Blood*, vol. 31, no. 2, pp. 234-241, 1968.
10. E. Nwanko, C. J. Durning, "Fluid property investigation by impedance characterization of quartz crystal resonators (2 parts)," *Sensors and Actuators A. Physical*, vol. 72, pp. 99-109, 1999.
11. B. Jakoby, M. Scherer, M. Buskies, H. Eisenschmid, "An automotive engine oil viscosity sensor," *IEEE Sensors Journal*, vol. 3, pp. 562-568, 2003.
12. S. Chien, J. Dormandy, E. Ernst, A. Matrai, "Clinical Hemorheology," Martinus Nijhoff Publishers, Dordrecht, 1987.
13. J. Wang, "Electrochemical Glucose Biosensors," *Chemical Reviews*, vol. 108, pp. 814-825, 2008.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches. The recitation of series of numbers with differing amounts of significant digits in the specification is not to be construed as implying that numbers with fewer significant digits given have the same precision as numbers with more significant digits given.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for measuring, at one or more time points, one or more properties or changes in properties of a fluid sample the device comprising:
   a chamber defining an internal volume of the device suitable for receiving and retaining the fluid sample;
   a plurality of layers, the plurality comprising at least a first layer below the chamber, at least a second layer above the chamber, and a substrate layer between the first and second layers, wherein:
   the substrate layer is linked to at least one suspended element located within the chamber;
   the suspended element is comprised of an insulating material and at least one continuous patterned conductive layer providing at least one electrically conductive path;
   the suspended element is linked to the substrate layer by at least two compliant structures located within the chamber;
   the suspended element and said at least two compliant structures are formed as part of the substrate layer;
   the suspended element is configured to oscillate upon application of an actuating signal to at least one said electrically conductive path, which runs fully across at least two of the said compliant structures and the suspended element;
   the suspended element and the at least two compliant structures are configured to have at least a first oscillation frequency and a second oscillation frequency, wherein the second oscillation is not a harmonic of the first oscillation;

oscillation at the first oscillation frequency induces a first acoustic field in the fluid sample with a first shear penetration depth smaller than a threshold value, wherein the threshold value ranges from 0.5 microns to 500 microns, and oscillation at the second oscillation frequency induces a second acoustic field in the fluid sample with a second shear penetration depth greater than the threshold value.

2. The device of claim 1, wherein the suspended element is configured to oscillate in-plane at the first oscillation frequency and the second oscillation frequency.

3. The device of claim 1, wherein the substrate layer comprises a non-conductive polymer constituting at least 50% by weight of the substrate layer.

4. The device of claim 1, wherein at least one electrically conductive path running across a suspended element consists essentially of one or more metals and/or conductive polymers.

5. A method of measuring one or more properties or changes in properties of a fluid sample using a device according to claim 1, the method comprising:

placing the fluid sample in the chamber of the device;

oscillating at least one suspended element of the device, wherein the oscillation causes a current or voltage in at least one of the electrically conductive paths of the device;

measuring the current or voltage at one or more times; and using one or more of the measurements of the current or voltage to calculate the one or more properties or changes in properties of the fluid sample;

wherein the method comprises in-plane and out-of-plane oscillating steps and at least two properties of the fluid sample chosen from continuous phase viscosity, bulk viscosity, viscoelasticity, density, and concentration of an analyte in the fluid sample are determined.

6. A device for measuring, at one or more time points, one or more properties or changes in properties of a fluid sample the device comprising:

a chamber defining an internal volume of the device suitable for receiving and retaining the fluid sample;

a plurality of layers, the plurality comprising at least a first layer adjacent to the chamber, at least a second layer adjacent to the chamber, and a substrate layer defined by one or both of the first and second layers, wherein:

the substrate layer is linked to at least one suspended element;

the suspended element is comprised of an insulating material and at least one continuous patterned conductive layer providing at least one electrically conductive path;

the suspended element is linked to the substrate layer by at least two compliant structures;

the suspended element and said at least two compliant structures are formed as part of the substrate layer;

the suspended element is configured to oscillate upon application of an actuating signal to at least one said electrically conductive path, which runs fully across at least two of the said compliant structures and the suspended element;

the suspended element and the at least two compliant structures are configured to have at least a first oscillation frequency and a second oscillation frequency, wherein the second oscillation is not a harmonic of the first oscillation;

oscillation at the first oscillation frequency induces a first acoustic field in the fluid sample with a first shear penetration depth smaller than a threshold value, wherein the threshold value ranges from 0.5 microns to 500 microns, and oscillation at the second oscillation frequency induces a second acoustic field in the fluid sample with a second shear penetration depth greater than the threshold value.

7. A device for measuring, at one or more time points, one or more properties or changes in properties of a fluid sample the device comprising:

a chamber defining an internal volume of the device suitable for receiving and retaining the fluid sample;

a plurality of layers, the plurality comprising at least a first layer adjacent to the chamber, at least a second layer adjacent to the chamber, and a substrate layer defined by one or both of the first and second layers, wherein:

the substrate layer is linked to at least one suspended element;

the suspended element is comprised of an insulating material and at least one continuous patterned conductive layer providing at least one electrically conductive path;

the suspended element is linked to the substrate layer by at least two compliant structures;

the suspended element and said at least two compliant structures are formed as part of the substrate layer;

the suspended element is configured to oscillate upon application of an actuating signal to at least one said electrically conductive path, which runs fully across at least two of the said compliant structures and the suspended element;

the suspended element and the at least two compliant structures are configured to have at least a lower oscillation frequency and a higher oscillation frequency, wherein the higher oscillation frequency is not a harmonic of the lower oscillation frequency, and at least one of the oscillations induces an acoustic field in the fluid sample with a penetration depth smaller than a threshold value, wherein the threshold value ranges from 0.5 microns to 500 microns.

* * * * *